(12) United States Patent
Srinivasan et al.

(10) Patent No.: US 11,056,239 B2
(45) Date of Patent: Jul. 6, 2021

(54) RISK-BASED MONITORING OF CLINICAL DATA

(71) Applicant: Remarque Systems, Inc., Chapel Hill, NC (US)

(72) Inventors: Badhri Srinivasan, Raleigh, NC (US); Joseph William Charles Goodgame, Chapel Hill, NC (US); Michael P. Arlotto, Chapel Hill, NC (US)

(73) Assignee: REMARQUE SYSTEMS, INC., Raleigh, NC (US)

( * ) Notice: Subject to any disclaimer, the term of this patent is extended or adjusted under 35 U.S.C. 154(b) by 179 days.

(21) Appl. No.: 15/756,261

(22) PCT Filed: Aug. 31, 2016

(86) PCT No.: PCT/US2016/049592
§ 371 (c)(1),
(2) Date: Feb. 28, 2018

(87) PCT Pub. No.: WO2017/040590
PCT Pub. Date: Mar. 9, 2017

(65) Prior Publication Data
US 2018/0240553 A1    Aug. 23, 2018

Related U.S. Application Data

(60) Provisional application No. 62/214,505, filed on Sep. 4, 2015.

(51) Int. Cl.
*G16H 50/30* (2018.01)
*G16H 40/67* (2018.01)
(Continued)

(52) U.S. Cl.
CPC ............ *G16H 50/30* (2018.01); *G16H 10/20* (2018.01); *G16H 10/60* (2018.01); *G16H 15/00* (2018.01);
(Continued)

(58) Field of Classification Search
CPC ... G06F 1/00–2221/2153; G16H 10/00–80/00; G06Q 10/00–2250/905; H04L 1/00–2463/146
See application file for complete search history.

(56) References Cited

U.S. PATENT DOCUMENTS 7,034,691 B1 *   4/2006   Rapaport ............... G06Q 10/10
                                                          340/573.1
8,706,537 B1 *   4/2014   Young .................... G06Q 10/10
                                                          705/7.11
(Continued)

FOREIGN PATENT DOCUMENTS

CA           2458772 A1 *   3/2003   ............. G06Q 10/10

OTHER PUBLICATIONS

Richard C. Zink, "Risk-Based Monitoring and Fraud Detection in Clinical Trials Using JMP and SAS," SAS Institute Inc. pp. 1-14 (Year: 2014).*

*Primary Examiner* — Elaine Gort
*Assistant Examiner* — Jonathan A. Szumny
(74) *Attorney, Agent, or Firm* — Coats & Bennett, PLLC

(57) ABSTRACT

A computing device generates an audit trail for monitoring clinical data. In particular, the computing device receives clinical data comprising patient data and investigator site data. The computing device accepts and rejects respective portions of the clinical data by applying a risk-based monitoring policy comprising one or more policy rules to the clinical data. The computing device generates an audit trail for the clinical data. The audit trail comprises the clinical
(Continued)

data and corresponding audit data. The audit data comprises identification of the accepted and rejected portions of the clinical data, identification of one or more of the policy rules of the risk-based monitoring policy used in the accepting and rejecting of the respective portions of the clinical data, and one or more timestamps corresponding to each of the accepting and rejecting of the respective portions.

19 Claims, 15 Drawing Sheets

(51) Int. Cl.
*G16H 40/63* (2018.01)
*G16H 10/60* (2018.01)
*G16H 15/00* (2018.01)
*G16H 80/00* (2018.01)
*H04L 9/32* (2006.01)
*G16H 50/70* (2018.01)
*G16H 10/20* (2018.01)

(52) U.S. Cl.
CPC ............ *G16H 40/63* (2018.01); *G16H 40/67* (2018.01); *G16H 50/70* (2018.01); *G16H 80/00* (2018.01); *H04L 9/3247* (2013.01)

(56) References Cited

U.S. PATENT DOCUMENTS

| | | | | |
|---|---|---|---|---|
| 9,092,964 | B1* | 7/2015 | Chan | G08B 21/02 |
| 10,453,563 | B2* | 10/2019 | Powell | G06Q 10/10 |
| 2002/0010679 | A1 | 1/2002 | Felsher | |
| 2004/0017475 | A1 | 1/2004 | Akers et al. | |
| 2005/0193043 | A1* | 9/2005 | Hoover | G06F 19/328 |
| 2005/0246204 | A1* | 11/2005 | Simon | G06Q 50/22 |
| | | | | 705/3 |
| 2006/0282291 | A1* | 12/2006 | Runciman | G06Q 50/24 |
| | | | | 705/3 |
| 2007/0106633 | A1* | 5/2007 | Reiner | G06F 19/321 |
| 2008/0222734 | A1* | 9/2008 | Redlich | G06F 21/577 |
| | | | | 726/26 |
| 2011/0261194 | A1* | 10/2011 | Udani | G06Q 10/10 |
| | | | | 348/135 |
| 2013/0262503 | A1* | 10/2013 | Newton | G06F 21/552 |
| | | | | 707/769 |
| 2013/0291060 | A1 | 10/2013 | Moore | |
| 2013/0346111 | A1* | 12/2013 | Goodgame | G06F 17/10 |
| | | | | 705/3 |
| 2014/0337086 | A1* | 11/2014 | Asenjo | G06Q 10/0635 |
| | | | | 705/7.28 |
| 2014/0372147 | A1* | 12/2014 | White | G16H 40/20 |
| | | | | 705/3 |
| 2019/0318100 | A1* | 10/2019 | Bhatia | H04L 63/1433 |

\* cited by examiner

RISK-BASED MONITORING OF CLINICAL DATA

RELATED APPLICATIONS

This application claims the benefit of U.S. Provisional Application No. 62/214,505, filed 4 Sep. 2015, the disclosure of all of which is incorporated by reference herein in its entirety.

TECHNICAL FIELD

The present disclosure relates to risk-based monitoring of clinical data in a computing device and, more particularly, to generating an audit trail for monitoring such clinical data.

BACKGROUND

Over the past decade the complexity and cost of clinical trials have increased while the productivity of biopharmaceutical and medical device R&D departments has decreased. Indeed, to take a drug from discovery through regulatory approval typically takes over a decade and costs billions of dollars (including the cost of failures). Candidate medicinal compounds have a high failure rate, with a very low percentage of the candidate compounds that enter clinical trials being approved by regulatory agencies, predominately due to poor safety or efficacy. Accordingly, the biopharmaceutical industry needs solutions for reducing cost and/or improving efficiency.

Clinical monitoring, in particular, is a significant source of clinical trial costs. Historically, the preferred method of clinical monitoring has been to perform source document verification (SDV) via on-site visits. Clinical Research Associates (CRAs) typically monitor clinical sites at the start of a study (i.e., through Start-Up Visits (SUVs)), at regular intervals during the study (i.e., through Interim Monitoring Visits (IMVs)), and at the end of the study (i.e., through Close-Out Visits (COVs)). The IMV follow a prescribed schedule and are typically on a 4- to 8-week frequency. This frequent on-site monitoring involves a large amount of SDV designed to ensure patient safety and generate quality data. This approach is a reactive and limited approach to identifying and preventing issues. In addition, this approach is labor and resource intensive for the drug developer as well as for the site being investigated. Since intense on-site monitoring does not guarantee identification of all subject safety or data quality issues, the associated high costs are disproportionate with the value gained.

One general approach to the high costs of on-site monitoring is to adopt risk-based monitoring (RBM). RBM is an approach that may be adopted for any type, phase (i.e., Phase 1 through Phase 4), and stage of trial. RBM also improves efficiency by changing the focus to central or off-site monitoring activities that may identify potential issues sooner than a monitoring strategy that relies primarily on on-site monitoring visits. The use of RBM allows on-site monitoring to be targeted at activities that cannot be assessed remotely. However, there are gaps in the technology that is presently available to support RBM.

SUMMARY

Disclosed herein are systems, methods, apparatus, and computer program products for risk-based monitoring (RBM) of clinical data.

Exemplary embodiments include a method, implemented by a computing device, for generating an audit trail for RBM. In some embodiments, the method comprises receiving clinical data comprising patient data and investigator site data. The method further comprises accepting and rejecting respective portions of the clinical data by applying a risk-based monitoring policy comprising one or more policy rules to the clinical data. The method further comprises generating an audit trail for the clinical data, the audit trail comprising the clinical data and corresponding audit data. The audit data comprises identification of the accepted and rejected portions of the clinical data. The audit data further comprises identification of one or more policy rules of the risk-based monitoring policy used in the accepting and rejecting of the respective portions of the clinical data. The audit data further comprises one or more timestamps corresponding to each of the accepting and rejecting of the respective portions.

In some embodiments of the method, applying the risk-based monitoring policy comprises applying a manual workflow to the clinical data.

In some embodiments of the method, applying the risk-based monitoring policy comprising at least one policy rule comprises applying a predefined automated workflow to the clinical data.

In some embodiments of the method, applying the risk-based monitoring policy comprising at least one policy rule comprises applying a machine-learning algorithm to the clinical data.

In some embodiments of the method, at least one policy rule comprises a policy rule that requires segmenting the clinical data into a relevant segment and a remainder, identifying the relevant segment as being comprised in one of the accepted and rejected portions, and timestamping one or more of the relevant segment and the remainder.

In some embodiments of the method, the audit data further comprises a digital signature certifying application of a corresponding policy rule identified in the audit data.

In some embodiments of the method, the patient data comprises, for at least one patient, demographic data, safety data, efficacy data and a medical history.

In some embodiments of the method, the investigator site data comprises productivity, quality, risk, and safety metrics for an investigated clinical site.

In some embodiments, the method further comprises configuring the risk-based monitoring policy by receiving the at least one policy rule from a user of the computing device.

In some embodiments of the method, the one or more of the policy rules comprises a policy rule that requires review of the clinical data by a medical reviewer and the generating of the audit trail for the clinical data.

In some embodiments of the method, the one or more of the policy rules comprises a policy rule that requires review of the clinical data by a central clinical reviewer and the generating of the audit trail for the clinical data.

In some embodiments of the method, the one or more of the policy rules comprises a policy rule that requires review of the clinical data by a statistical reviewer and the generating of the audit trail for the clinical data.

Other embodiments comprise a computing device for generating an audit trail for RBM. In some embodiments, the computing device comprises interface circuitry and processing circuitry communicatively coupled to the interface circuitry. The processing circuitry is configured to receive clinical data comprising patient data and investigator site data via the interface circuitry. The processing circuitry is further configured to accept and reject respective portions of the clinical data by applying a risk-based monitoring policy comprising one or more policy rules to the clinical data. The processing circuitry is further configured to generate an audit trail for the clinical data, the audit trail comprising the clinical data and corresponding audit data. The audit data comprises identification of the accepted and rejected portions of the clinical data. The audit data further comprises identification of one or more policy rules of the risk-based monitoring policy used in the accepting and rejecting of the respective portions of the clinical data. The audit data further comprises one or more timestamps corresponding to each of the rejecting of the accepting and rejecting of the respective portions.

In some embodiments, the processing circuitry is further configured to send the audit trial to a user via the interface circuitry.

Various embodiments of the computing device are configured to perform any of the methods described herein.

Other embodiments comprise a computer program product stored in a non-transitory computer readable medium for controlling a programmable computing device. The computer program product comprises software instructions that, when executed on the programmable computing device, cause the programmable computing device to perform any of the methods described herein.

DETAILED DESCRIPTION

As will be described in detail below, aspects of the present disclosure may be implemented entirely as hardware units, entirely as software modules (including firmware, resident software, micro-code, etc.), or as a combination of hardware units and software modules. For example, embodiments of the present disclosure may take the form of a non-transitory computer readable medium storing software instructions in the form of a computer program that, when executed on a programmable device, configures the programmable device to execute the various methods described below.

For clarity in understanding the disclosure below, to the extent that "one of" a conjunctive list of items (e.g., "one of A and B") is discussed, the present disclosure refers to one (but not both) of the items in the list (e.g., an A or a B, but not both A and B). Such a phrase does not refer to one of each of the list items (e.g., one A and one B), nor does such a phrase refer to only one of a single item in the list (e.g., only one A, or only one B). Similarly, to the extent that "at least one of" a conjunctive list of items is discussed (and similarly for "one or more of" such a list), the present disclosure refers to any item in the list or any combination of the items in the list (e.g., an A only, a B only, or both an A and a B). Such a phrase does not refer to one or more of each of the items in the list (e.g., one or more of A, and one or more of B).

Figure 1:
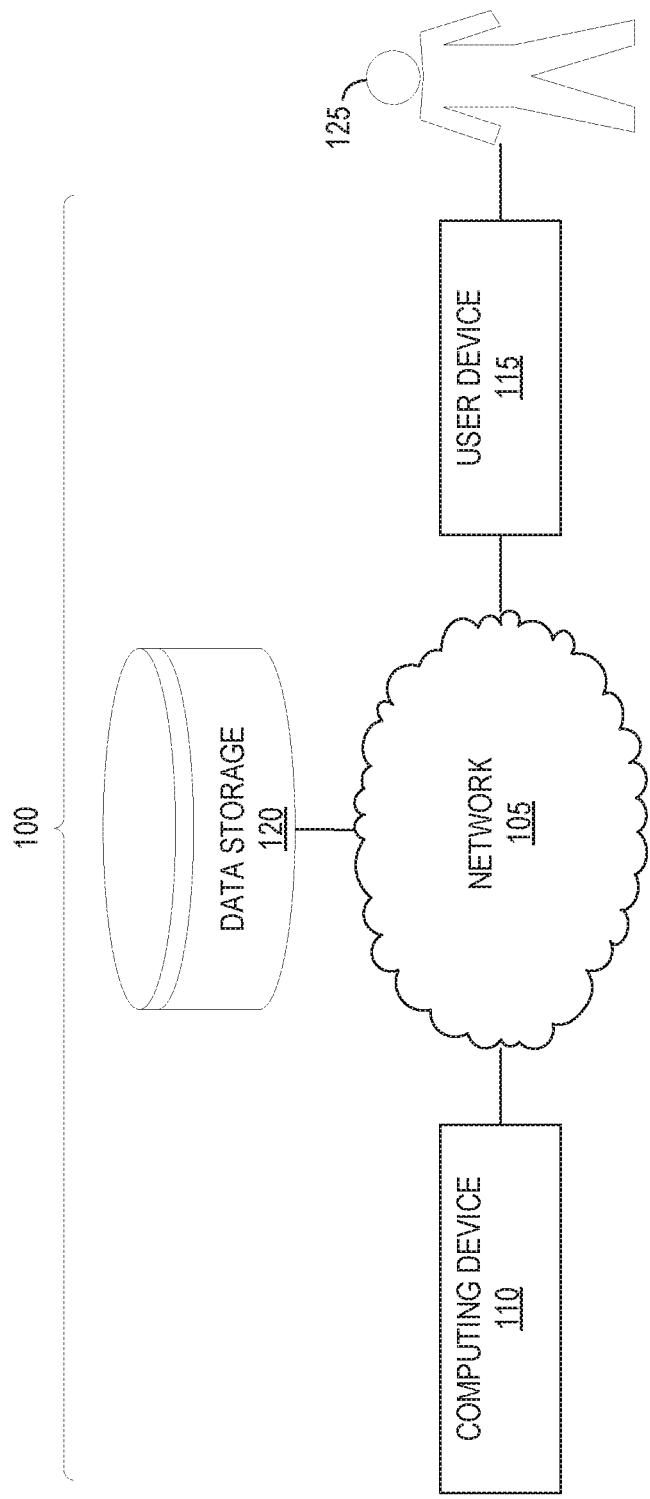
FIG. 1 is a block diagram illustrating an example system, according to one or more embodiments.

Embodiments of the present disclosure generally relate to systems, methods, apparatus, and computer program products for risk-based monitoring (RBM). FIG. 1 illustrates an exemplary system 100 for RBM. The system 100 includes a computing device 110, a user device 115, a network 105, and data storage 120. The computing device 110, user device 115, and data storage 120 are each communicatively connected to, and exchange signals with each other via, the network 105. One or more users 125 access the system 100 via the user device 115. Although only one user device 115 is illustrated in FIG. 1, other embodiments may include additional user devices 115 that may each be used by one or more of the users 125. Other embodiments may include a computing device 110 that also performs the functions of the user device 115 and/or data storage 120, i.e., without communicating over network 105.

Typical examples of the computing device 110 include a server computer and/or server cluster. Other examples of the computing device 110 include a personal computer, a laptop computer, a desktop computer, a workstation, a smartphone, a tablet computer, a wearable computer, a smart appliance, network attached storage, and/or a storage area network.

Typical examples of the user device 115 include a personal computer, a laptop computer, a desktop computer, a workstation, a smartphone, a tablet computer, a wearable computer, and/or a smart appliance. Other examples of the user device 115 include a server computer, a server cluster, network attached storage, and/or a storage area network.

The network 105 includes one or more physical devices and/or signaling mediums capable of exchanging communication signals with the computing device 110 and user device 115. Examples of such a network 105 include (but are not limited to) one or more of: the Internet (or a portion thereof); one or more local area networks; one or more wireless networks; one or more cellular networks; one or more Internet Protocol-based networks; one or more Ethernet networks; one or more optical networks; and/or one or more circuit switched networks. Such a network 105 may comprise any number of networking devices such as routers, gateways, switches, hubs, firewalls, and the like (not shown) supporting the exchange of such communication signals.

Examples of the data storage 120 include a storage area network (SAN), a network attached storage (NAS) server, a Redundant Array of Independent Disks (RAID) array, a solid state drive, and a hard disk drive. Although the data storage 120 and computing device 110 illustrated in FIG. 1 are connected to each other via the network 105 (e.g., as part of a cloud-based solution), the data storage 120 and computing device 110 may instead be collocated within the same computing platform.

Figure 2:
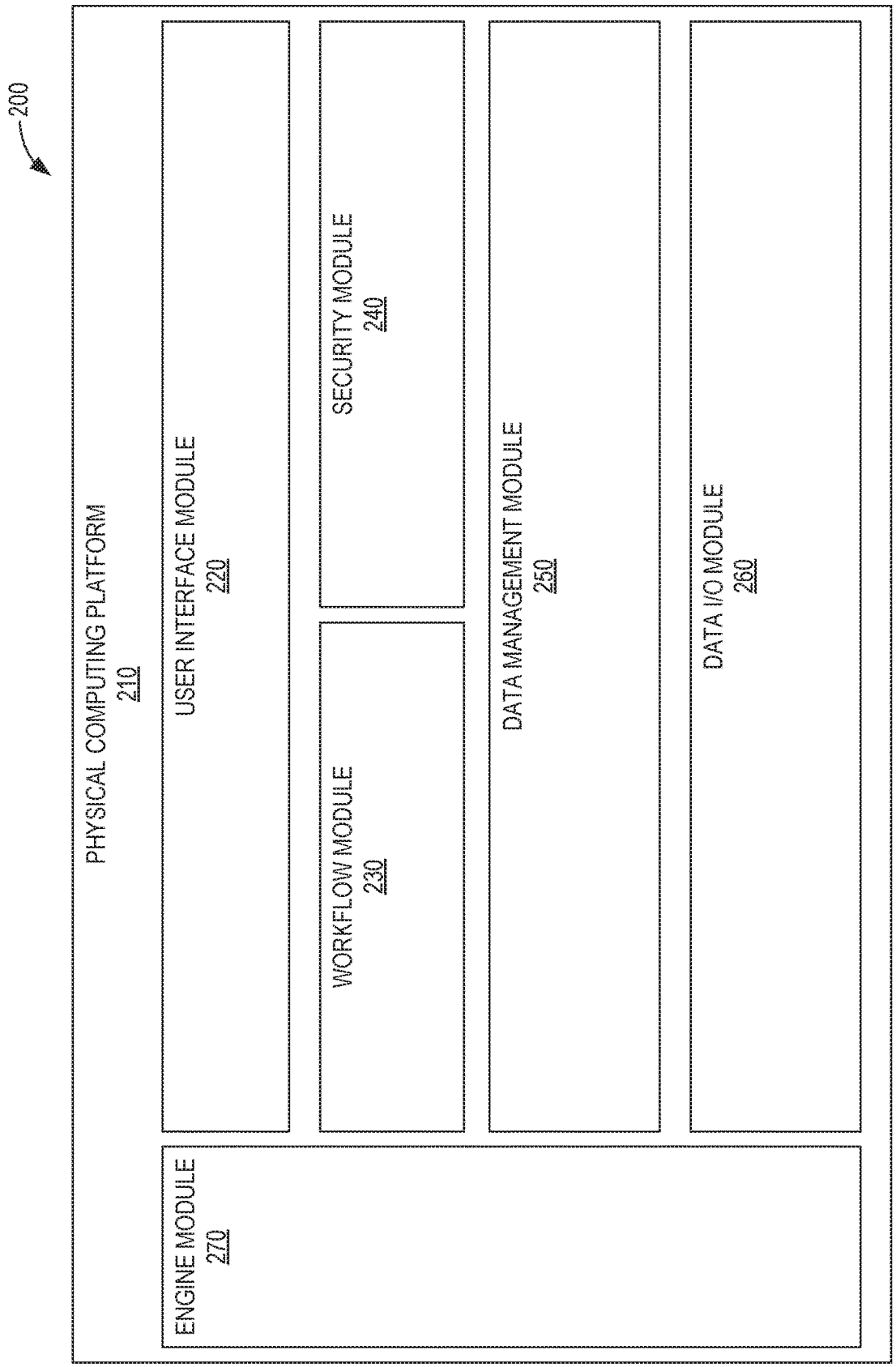
FIG. 2 is a block diagram illustrating an example physical architecture, according to one or more embodiments.

Various software modules useful for implementing a physical architecture for the system 100 may be stored in the data storage 120, and executed on the computing device 110, the user device 115, or both in coordination. FIG. 2 illustrates an example of such a physical architecture 200. The physical architecture 200 comprises a physical computing platform 210 (e.g., the computing device 110, the user device 115, or both in combination) configured to execute, for example, a user interface (UI) module 220, a workflow module 230, a security module 240, a data management module 250, a data input/output (I/O) module 260 and engine module 270. Other modules may additionally or alternatively be included, according to other embodiments.

Generally, the physical architecture 200 may identify risks, drive critical variables, triggers, thresholds, and actions within the system 100. The physical architecture 200 may also link to critical documents such as a clinical protocol, Investigator Brochure, clinical monitoring plan, and data management plan (not shown), so that an Integrated Quality and Risk Management Plan (IQRMP) may be maintained.

Figure 3:
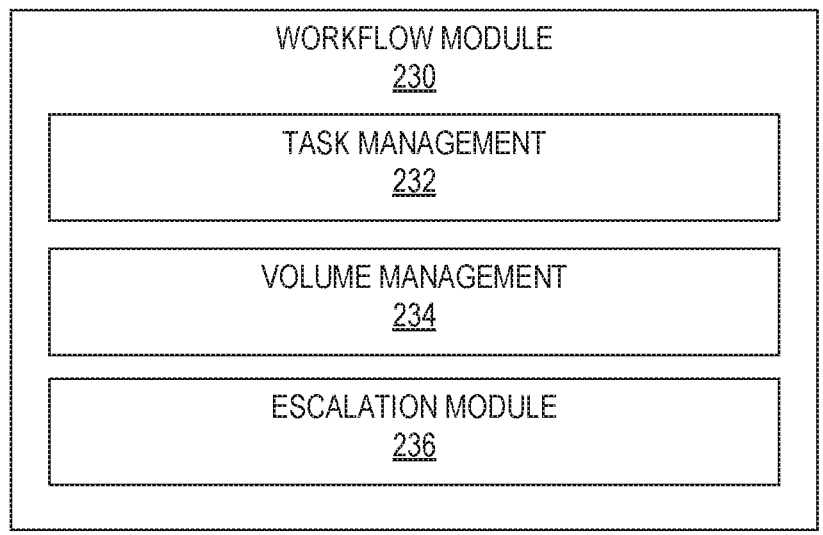
FIG. 3 is a block diagram illustrating an example workflow module, according to one or more embodiments.

FIG. 3 illustrates an example of the workflow module 230. Generally, the workflow module 230 may handle the linking of processing steps to be performed on transactions with the physical architecture 200. In the example of FIG. 3, the workflow module 230 includes a task management module 232, volume management module 234, and/or an escalation module 236. The task management module 232 may be configured to manage tasks, either within or externally to the context of the physical architecture 200. The volume management module 234 may be configured to handle data duplication, archiving, and overall storage/volume management tasks. The escalation module 236 may be configured to raise alerts, notify administrators, and enact action plans in response to detected issues. Other functions within the workflow module 230 may additionally or alternatively be included, according to other embodiments.

Figure 4:
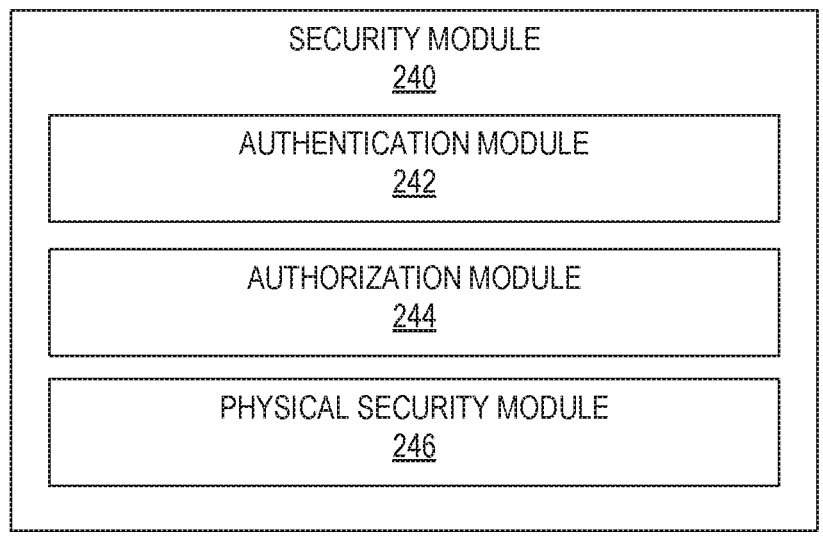
FIG. 4 is a block diagram illustrating an example security module, according to one or more embodiments.

FIG. 4 illustrates an example of the security module 240. Generally, the security module 240 may perform authorization and authentication services, thereby ensuring physical and application level security. To do so, the security module 240 may comprise an authentication module 242, an authorization module 244, and a physical security module 246. The authentication module 242 may be configured to authenticate the identity of user 125. The authorization module 244 may be configured to determine whether the user 125 is allowed to access the physical architecture 200 or particular services or functions provided thereby. The physical security module 246 may be configured to determine whether the system 100 has been physically accessed and/or whether such physical access is permissible. Other functions within the security module 240 may additionally or alternatively be included, according to other embodiments.

In some embodiments, this security module 240 takes advantage of the services of a third-party hosting provider. In addition, application security may be performed via Active Directory authentication, Secure Sockets Layer (SSH), and token management. The security module 240 may also utilize secure web service access driven by user credentials at a protocol and permission level. Capabilities within the physical architecture 200 may be granted via a permission set to particular roles within the system 100, or to a specific user regardless of what role that user 125 may be assigned to.

The workflow and security modules 230, 240 may, for example, be implemented by the .Net framework. This .Net framework may provide users 125 with access to the rules, workflow management, security, services, and enable business-to-business transfers of data.

Figure 5:
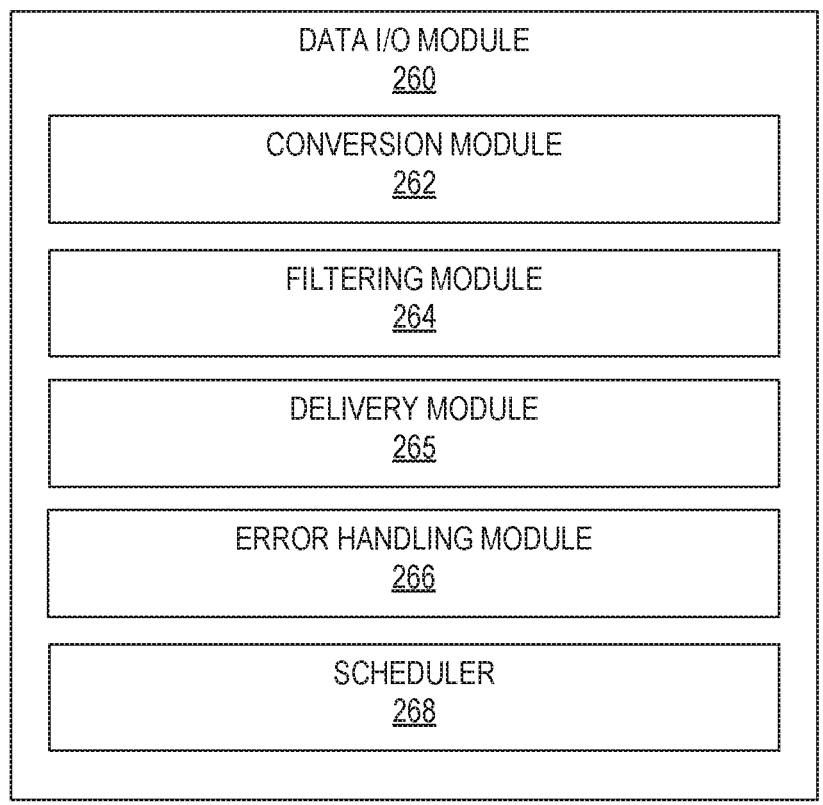
FIG. 5 is a block diagram illustrating an example data input/output module, according to one or more embodiments.

FIG. 5 illustrates an example of the data I/O module 260. The data I/O module 260 may be configured to consume clinical data from one or more external data sources (not shown). The data I/O module 260 may comprise a conversion module 262, a filtering module 264, a delivery module 265, an error handling module 266, and/or a scheduler 268. Generally, the data I/O module 260 may convert and/or filter data, schedule data flows, and handle errors. The data I/O module 260 may also provide Application Programming Interfaces (APIs) over both flat file and service architecture for all patient, site, and protocol domains. APIs may also be provided for supplying documentation and templates, such as documents commonly used for reference in the system 100.

More particularly, the conversion module 262 may be configured to convert data received or sent by the physical computing platform 210. The filtering module 264 may be configured to remove extraneous data from the data of relevance to one or more users 125 or clinical studies. The delivery module 265 may be configured to provide File Transfer Protocol (FTP) and/or Web Services (WS) based access to clinical data. The error handling module 266 may be configured to detect and respond to errors in the data. The scheduler 268 may be configured to arrange for certain tasks (e.g., managed by the workflow module 230) to be performed on the data and/or to manage data flow into and out of the physical computing platform 210, e.g., at particular times and/or in response to particular events. Other functions within the data I/O module 260 may additionally or alternatively be included, according to other embodiments.

Figure 6:
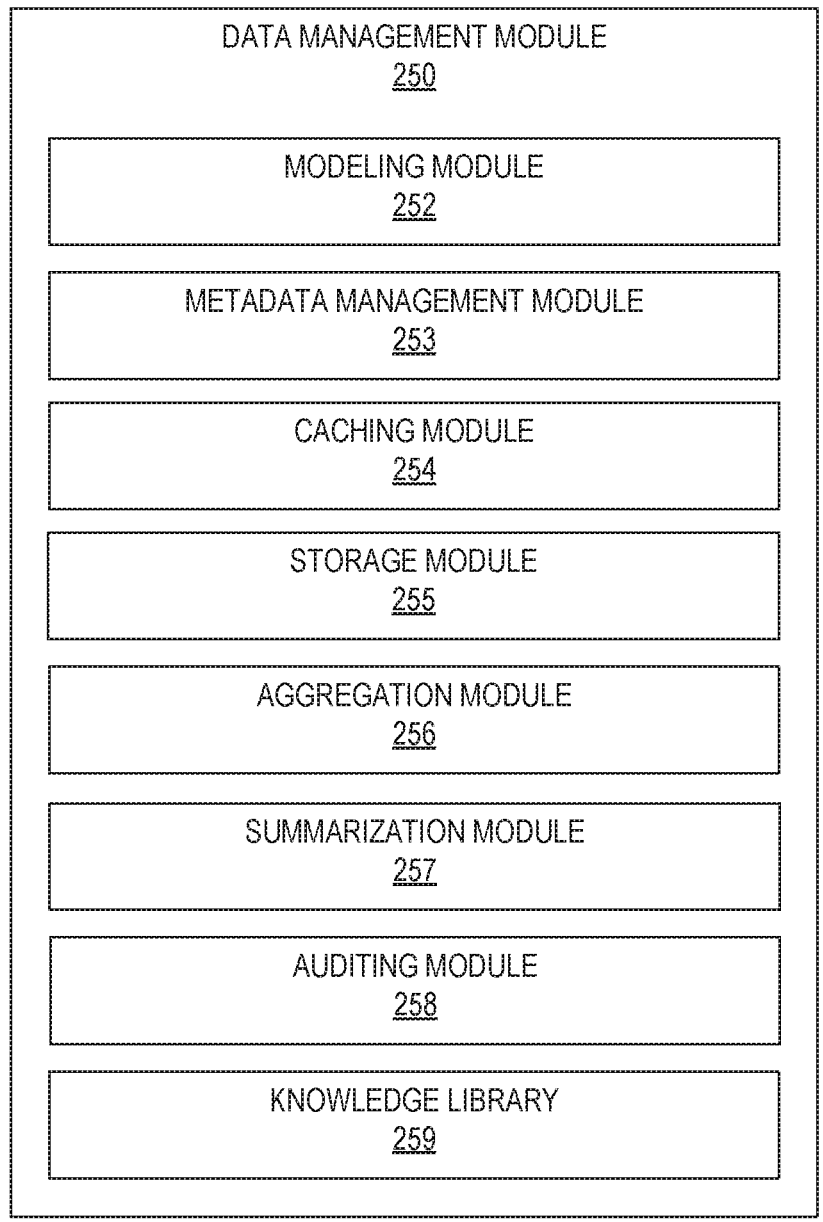
FIG. 6 is a block diagram illustrating an example data management module, according to one or more embodiments.

FIG. 6 illustrates an example of the data management module 250. Generally, the data management module 250 may handle the security of data ingested by the data I/O module 260, as well as store, cache, aggregate, summarize, model, track, and audit data. In particular, the data management module 250 may support predictive analytics through machine learning algorithms as well as classical statistical models. One such model may be based on similar patients/sites/protocol, and is assisted with human training to provide predictive capabilities when looking at patient/site data. By accumulating data either at the protocol or program level, these models in the data management module 250 anticipate behavior due to specific risk indicators. Other example models include pre-loaded standard statistical models such as Principle Component Analysis, Mahalanobis Distance analysis, Regression Models, and Benford's Law, among others. The output from such models may be made available to a statistical reviewer through the statistical monitor of the UI module 220, as will be explained in greater detail below. Further, users 125, such as a statistical reviewer, may be permitted to load their own models, including statistical and/or mathematical models, into the system 100 so that any analysis preferred by such user 125 may be readily available within the system 100. Approval to make these imported models available for use within the physical architecture 200 may be required, according to various embodiments.

The data management module 250 may also comprise a knowledge library 259 designed to store information at the Therapeutic, Disease, Compound Class, and Compound specific levels along with feedback from human teaching. This knowledge library 259 may be used to enhance predictive analytics, configure studies, and pre-identify risk indicators and critical variables.

The data management module 250 may comprise a modeling module 252, a metadata management module 253, a caching module 254, a storage module 255, an aggregation module 256, a summarization module 257, and/or an auditing module 258, according to embodiments. The modeling module 252 may be configured to apply various statistical models to the clinical data. The metadata management module 253 may be configured to generate and/or analyze metadata derived from the clinical data. The caching module 254 may be configured to control the manner and/or frequency in which data is cached. The storage module 255 may be configured to control how, when, and/or which data is stored. The aggregation module 256 may be configured to compile data into groups. The summarization module 257 may be configured to determine the overall characteristics of groups of data. The auditing module 258 may be configured to generate an audit trail of the data and/or the actions taken upon such data by the physical architecture 200. Other functions within the data management module 250 may additionally or alternatively be included, according to other embodiments.

The data management module 250 and data I/O module 260 may employ a distributed model (e.g., via a HADOOP ecosystem) to ingest various types and formats of data from various data sources and store the data in their native formats. This base data platform may further provide scalability, data format agnostic capability, and service the machine learning and visualization functions of the physical architecture 200. The system 100 may accept data from Electronic Data Capture (EDC) systems, Clinical Data Management Systems (CTMS), and clinical laboratory systems. Embodiments may be agnostic to the type and format of the data, and agnostic to the data delivery mechanism. The security of these data delivery mechanisms may be utilized using only secured services such as Secure Shell (SSH) File Transfer Protocol (SFTP), Secure Hypertext Transfer Protocol (HTTPS), and/or secure Web Services, for example. Embodiments may be a hosted cloud-based Software-as-a-Service (SaaS) offering as part, or an in-house deployment on a customer-specific cloud, with or without data warehousing. Further, an API may permit such data to be extracted and transmitted, if required, using a standardized data format. The data ingestion module and data tier may together regulate the quality of the data used for role-based reviews, as well as control data streaming or batching. These roles will be discussed in greater detail below.

Figure 7:
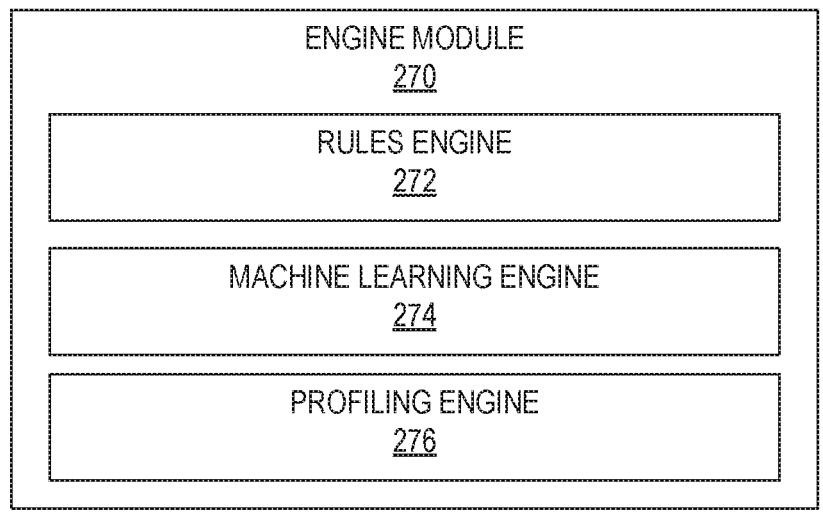
FIG. 7 is a block diagram illustrating an example engine module, according to one or more embodiments.

FIG. 7 illustrates an example of the engine module 270. Generally, the engine module 270 may interoperate with any or all of the other modules, according to embodiments. In particular, the engine module 270 may include one or more of a rules engine 272, a machine learning engine 274, or a profiling engine 276.

The rules engine 272 may be configured to execute one or more rules, e.g., in a planned, scheduled, and/or ordered fashion. The rules enable the various workflows to be triggered. The machine learning module 274 may make use of the data of the data management module 250, and the rules, in order to trigger workflows based on whether the data conforms or is an outlier within one or more data models. The machine learning module 274 may also be utilized, in combination with the aforementioned statistical models, by a profiling engine 276 (as will be discussed in greater detail below).

Figure 8:
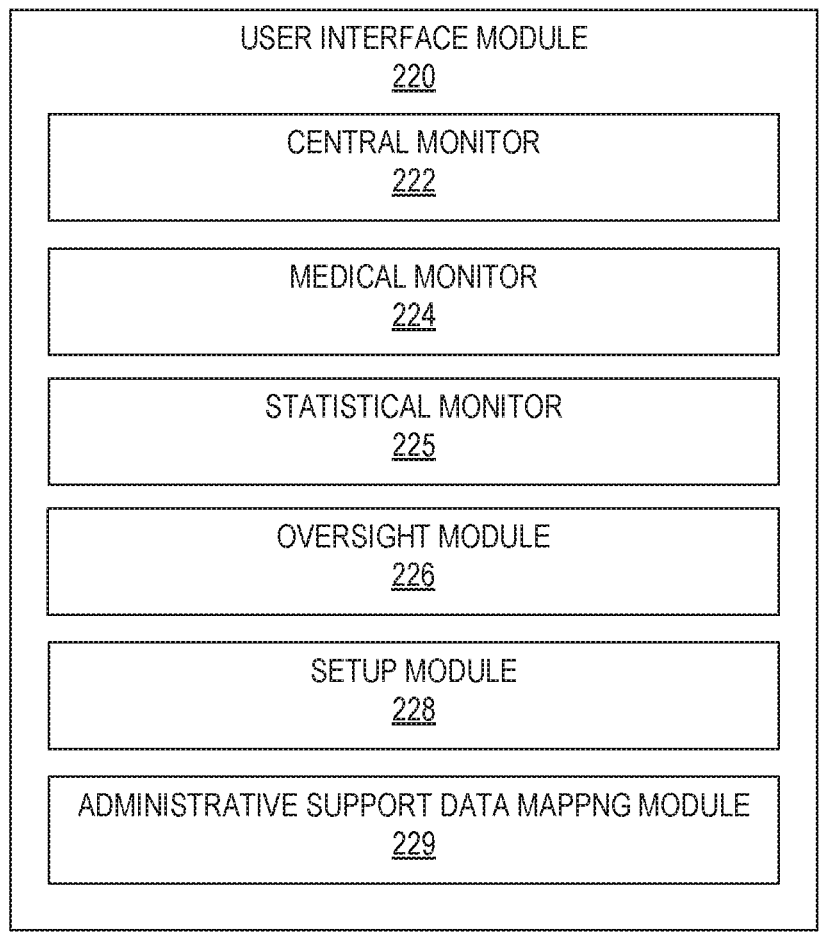
FIG. 8 is a block diagram illustrating an example user interface module, according to one or more embodiments.

FIG. 8 illustrates an example of the UI module 220. Generally, the UI module 220 may provide visualizations for any or all data, including any or all risk parameters and critical variables, within the physical architecture 200. These visualizations may be interactive and designed for the user 125 to quickly narrow their focus to problem areas (e.g., patients, sites, time points). Further, these visualizations may be available for cross-sectional data (at a point in time, e.g., at a visit), repeated measures (over time, e.g., trends across visits) and as multivariate comparisons (comparison of two or more variables at a time to understand interactions). Further, the UI module 220 may expose a visualization API that allows the user 125 to import their own visualizations for approval and use within the system 100. Such visualizations may be provided in the form of a website and/or graphics, according to embodiments. For example, the UI module 220 may respond to Hypertext Transfer Protocol (HTTP) requests from the user device 115 with a website and/or graphics content. The UI module 220 may additionally or alternatively be responsible for portability and customization features provided to the user 125 using, for example, Angular JS, Bootstrap, D3, and/or HTML5. The UI module 220 may also include (or work closely with) a services tier that provides RESTful services to the user 125 interfacing with the physical architecture 200 via the website (or via the UI module 220, more generally).

The UI module 220 may comprise several sub-modules, such as a central monitor 222, a medical monitor 224, a statistical monitor 225, an oversight module 226, a setup module 228, and/or an administrative support data mapping module 229.

The setup module 228 presents an interface to the user 125 for protocol and program setup that allows for selection, configuration, and/or maintenance of critical variables, risks, safety parameters, thresholds, and triggers by the user 125. The setup module 228 may also expose configuration capabilities that allow the user 125 to change the thresholds for selected parameters, adjust weightings, add/remove new/different critical variables, and/or set default actions for performance, quality, risk, and safety parameters. The setup module 228 may also proceed through checklists for the various roles within the system 100 that drive components of workflow activities within the system 100. Information from the data storage 120 and/or from other modules may be used to automatically populate sections within the setup interface exposed via the user device 115. The UI module 220 may also allow for linking and embedding plans that may be required for the IQRMP (e.g., the Clinical Management Plan (CMP), Sustainable Action Plan (SAP), and/or Data Management Plan (DMP)), thus allowing the user 125 to maintain the IQRMP.

In addition, the setup module 228 provides configurable rules for data quality (including the ability to exclude select datasets or data fields, for example, those datasets or variables that may causing un-blinding of the data) and data streaming allowing the user 125 to determine quality thresholds for decision making, as well as the ability to custom configure the cadence of data intake, whether streaming or in batches. Although the physical architecture 200 may allow the user 125 to configure any or all of the RBM parameters at setup, the RBM parameters may also be modified, updated, and/or changed during the course of a clinical trial, thereby giving flexibility to the user 125 and the ability to incorporate learnings and findings as a trial is progressing. Audit trail and version control may be maintained for all setup tasks.

The central monitor 222, medical monitor 224, and statistical monitor 225 may be designed for users 125 performing respective RBM roles, and each may have one or more workflows that convert findings into trackable actions. These modules 222, 224, 225 may be designed specifically for their respective roles, and therefore may provide certain capabilities that may only be accessed by users 125 fulfilling those particular roles.

For example, the central monitor 222 may be a module that enables a user 125 performing a central monitor role to review site-level data for performance, quality, risk, and safety. The central monitor 222 may also enable the user 125 to prioritize and triage workflow actions 444, manages how CRAs resolve actions, and follows-up on pending/unresolved actions.

The medical monitor 224 may be designed for users 125 performing a medical monitor role. The medical monitor 224 may enable a user 125 to review patient level data for safety, protocol congruence, data quality and consistency.

The statistical monitor 225 may be designed for users 125 performing a statistical monitor role. The statistical monitor 225 may enable a user 125 to investigate site and patient data for procedural errors, recording errors, and fraud. Other capabilities that are not specific to individual monitor roles may be shared across roles.

In addition to the monitor roles, the oversight module 226 may be designed for users 125 that are performing executive oversight. Thus, the oversight module 226 may produce visualizations that contain general study/program status, specific study performance metrics, role-specific metrics, and overall study health score and risks.

Although the physical architecture 200 has been discussed above according to the particular modules illustrated in FIGS. 2 through 8, the functions described above may be performed by fewer, additional, or different modules as appropriate.

Figure 9:
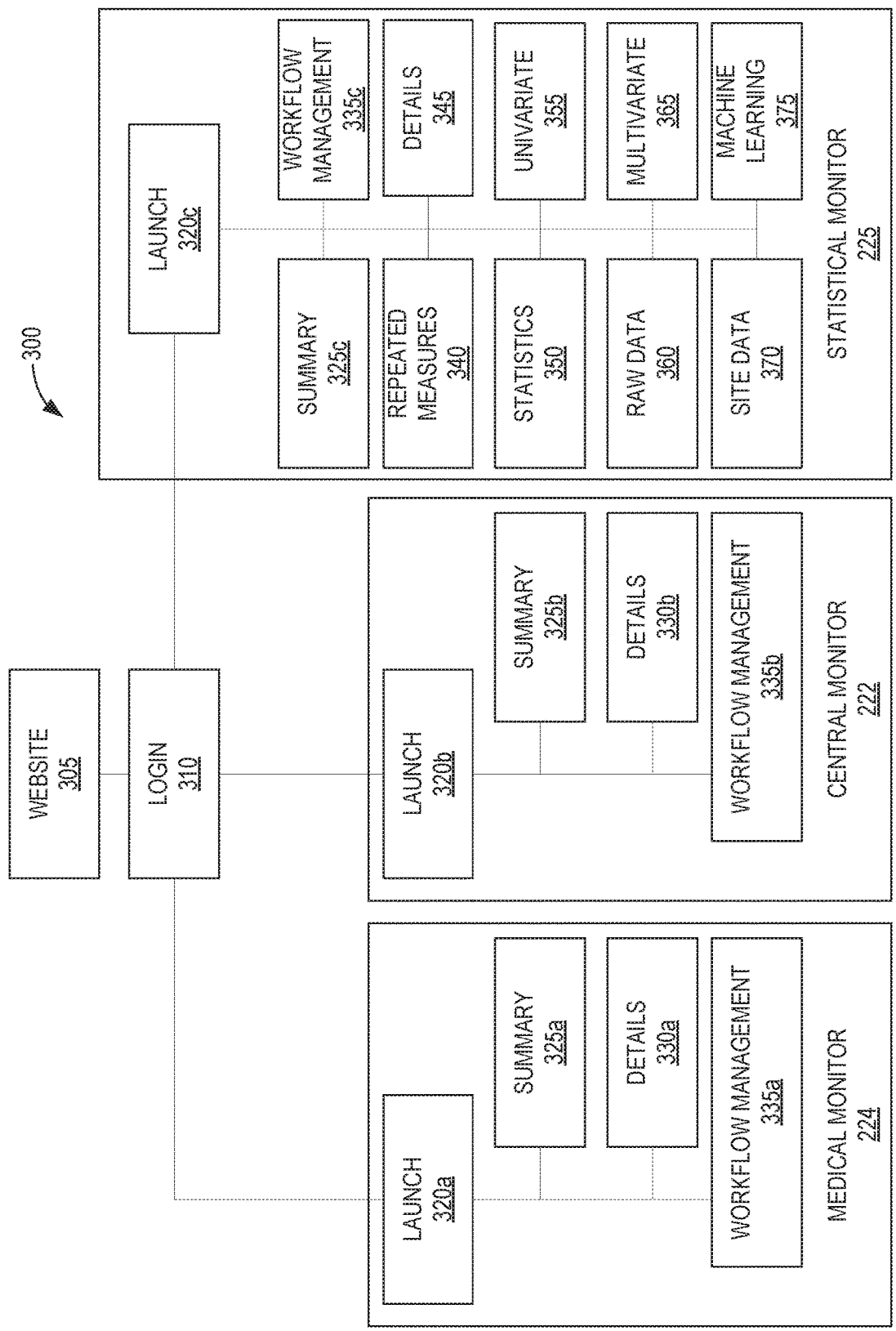
FIG. 9 is a block diagram illustrating an example application flow, according to one or more embodiments.

FIG. 9 illustrates an example initial application flow 300 that may be supported by the physical architecture 200 to provide role-based capabilities, shared capabilities, and permission-based capabilities to one or more users 125. A user 125 accesses the physical architecture 200 via a website 305, as previously discussed. The user 125 may then log in by providing appropriate credentials at a login screen 310, such that they may be authenticated by the security module 240, and accorded permissions commensurate with their role, e.g., by providing a username and password.

The users 125 role may be a medical monitor role, a central monitor role, or a statistical monitor role, as previously discussed. Accordingly, the physical architecture 200 may launch 320a-c the medical, central, or statistical monitor 224, 222, 225 upon login in accordance with that users 125 role in order to provide certain role-based capabilities to the user 125.

For example, each monitor 224, 222, 225 may present the user 125 with a respective summary page 325a-c, detailed page 330a-c, and access to workflow management 335a-c. In these and other pages and/or screens, particular monitors may present the user 125 with features that are unique to their corresponding role. For example, the statistical monitor 225 may enable the user 125 to perform univariate or multivariate analysis 355, 365, examine raw data 360, evaluate site data 370, examine or configure repeated measures 340, use or configure the machine learning capabilities 375 of the physical architecture 200, and perform other statistical functions 350.

In addition to the role-based features discussed above, each role may be permitted to access the shared capabilities of the physical architecture 200. Such shared capabilities may include access to visualizations, table and grid functions, printing, workflow creation/management, filtering/stratifying data, exporting data, accessing documents and checklists, sharing information, navigating through the interface, and other features. Further, as previously mentioned, certain features may be granted to particular users 125 based on their particular permissions. For example, a user 125 may be specifically granted executive oversight, or setup capabilities, based on their permissions.

Figure 10:
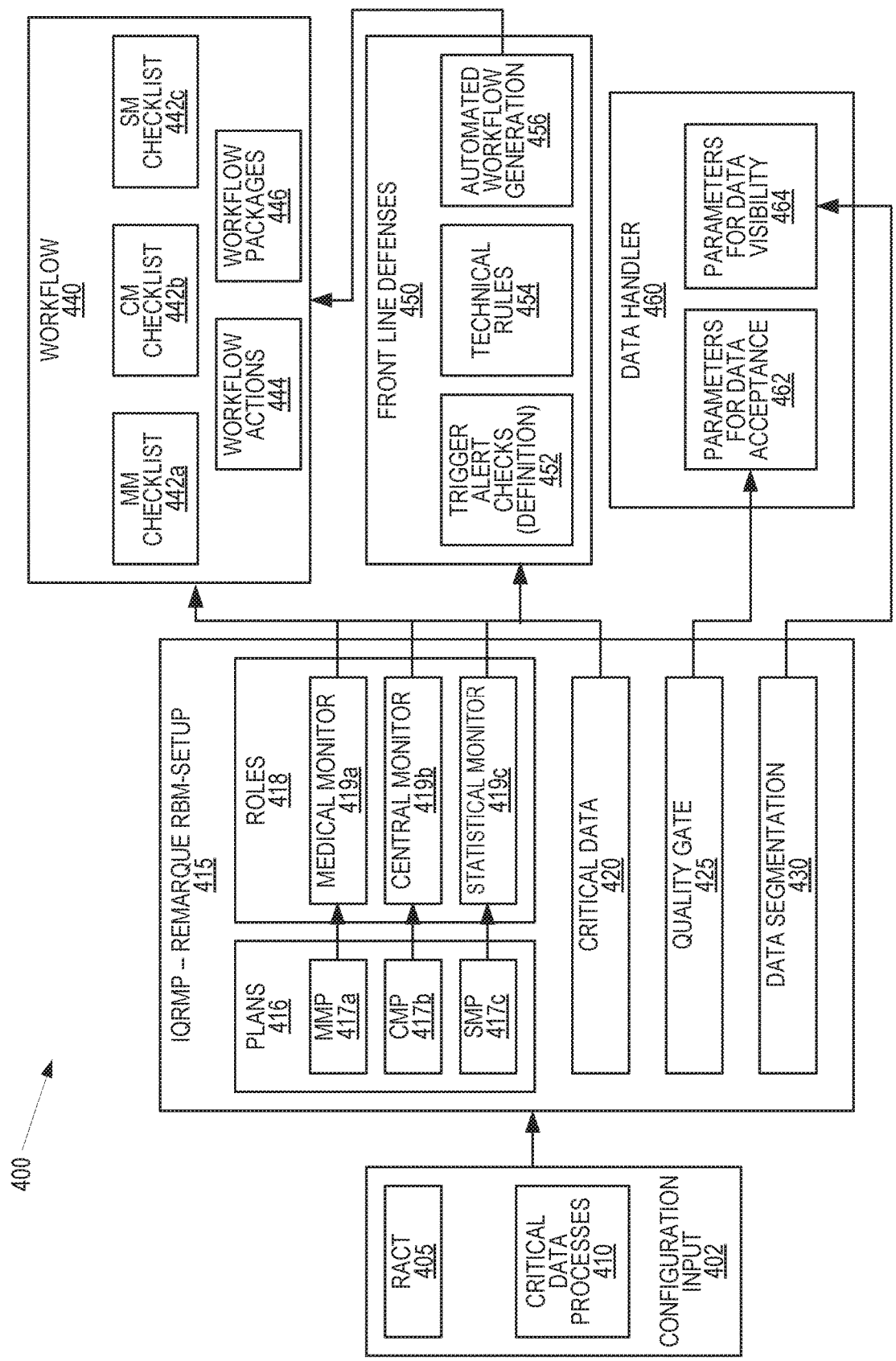
FIG. 10 is a block diagram illustrating another example application flow, according to one or more embodiments.

FIG. 10 illustrates another example application flow 400 implemented by the physical architecture 200. The application flow 400 starts from a given configuration input 405, which feeds IQRMP setup 415, which feeds the frontline defenses (FLDs) 450, and data handler 460. The above-discussed profiling engine 276 and UI module 220 may also work on the data. The FLDs 450, together with the IQRMP, feed workflows 440, which may be role-based.

The configuration input 402 comprises risk assessment/categorization tool (RACT) input 405 and Critical Data and Processes (CDP) 410. The RACT input 405 may be used in setup to establish a plan 416 for each of the roles 418. For example, the RACT input may be used to establish a Medical, Central, and Statistical Monitoring Plan 417a-c corresponding to medical, central, and statistical monitoring roles 419a-c, respectively.

The CDP 410 may comprise those patient and site parameters that are deemed to be critical to the study and require robust remote monitoring. The RACT input 405 and CDP 410 may be editable during setup. The critical data 420 in particular may be used by one or more of the aforementioned roles to go through a workflow checklist 442a-c that corresponds to their role 418.

The critical data 420 also is used by the FLDs 450 in order to trip triggers, generate alerts, and perform checks 452. The FLDs 450 may comprise technical rules 454 for application of these triggers, alerts and checks 452. Further, the FLDs 450 may comprise automated workflow generation functionality 456 that creates workflow actions 444 and workflow packages 446 used in role-based and/or automated workflows.

A quality gate 425 and data segmentation 430 are also configured during setup. The quality gate 425 informs the data handler 460 of the parameters for data acceptance 462. The data segmentation 430 informs the data handler 460 of the parameters for data visibility 464. The above-discussed profiling engine 276 may operate on the data in view of the parameters for data acceptance and/or visibility 462, 464 according to one or more machine learning algorithms and/or a knowledge library 259 as previously discussed.

The RACT input 405 may initially be built into the setup module 228, allowing the user 125 to complete and maintain risk assessment/categorization within the physical architecture 200. The RACT input 405 may be editable and designed for completion by various groups of experts who may be working on different sections of the RACT input 405. Relevant portions of the user interface for RACT setup may be automatically populated from various sections of the RACT input 405. For example, sections pertaining to a particular functional plan, or pertaining to risk mitigation, may be automatically populate a corresponding section within the RACT setup user interface.

CDP 410 may be identified as part of RACT setup and/or completion. The CDP setup user interface may be populated with identified CDP. Entries within the CDP setup may be editable and designed for completion by various groups of experts who may be working on different sections of the CDP. Critical Data checks may become part of the FLD automated checks within the physical architecture 200. As previously discussed, data segmentation 430 within the setup module 228 allows the user 125 to define and specify the data segments for a study. The Quality Gate 425 section within the setup module 228 allows the user 125 to define and specify the conditions and details for one or more tiers of quality management.

The medical monitoring checklist 442a of the setup module 228 may specify the various checks that need to be performed by the Medical Monitor 224. These checks can be specified by the user 125 and/or pre-populated from the RACT input 405. These checks can be modified/deleted/added to during the course of a study to reflect changing priorities as well as learnings from the trial. The Knowledge Library 259, over time, may accumulate and maintain program, compound, therapeutic area, and disease-specific Medical Monitor 224 checks to become part of a Medical Monitor Suggestion Engine.

The central monitoring checklist 442b specifies the various checks that need to be performed by the Central Monitor 222. These checks can be specified by the user 125 and/or pre-populated from the RACT input 405. These checks can be modified/deleted/added to during the course of a study to reflect changing priorities as well as learnings from the trial. The Knowledge Library 259, over time, may accumulate and maintain program, compound, therapeutic area, and disease-specific Central Monitor 222 checks to become part of a Central Monitor Suggestion Engine.

In addition, the setup module 228 may comprise a user interface for setting up the statistical monitoring checklist 442c. The statistical monitoring checklist 442c specifies the various checks that need to be performed by the Statistical Monitor 225. These checks can be specified by the user 125 and/or pre-populated from the RACT input 405. These checks can be modified/deleted/added to during the course of a study to reflect changing priorities as well as learnings from the trial. The Knowledge Library 259, over time, may accumulate and maintain program, compound, therapeutic area, and disease-specific Statistical Monitor 225 checks to become part of a Statistical Monitor Suggestion Engine.

In addition, the setup module 228 may comprise a user interface for setting up risk indicators. Risk Indicators may be site-level parameters for assessing site performance, quality, risk, and safety. These risk indicators may be compliant with externally-provided requirements. The type of risk indicator, weighting, algorithm for establishing thresholds, specific attribute may each be user-configurable and editable at the start of a study and at any point during the course of a study. The Knowledge Library 259 may, over time, accumulate and maintain program, compound, therapeutic area, disease, and country specific risk indicators to become part of a Risk Indicator Suggestion Engine.

For example, the setup module 228 may allow the user 125 to specify, for each investigator site, the expected IMV interval as part of the configuration input 402. For example, the user 125 may specify an IMV interval as being high (such as once every 6 weeks), medium (such as once every 12 weeks), and low (such as once every 24 weeks). Based on this setting, the physical architecture 200 may calculate the expected number of interim monitoring visits required for each site through to study completion. This may allow the user 125 to compare expected IMV usage versus actual to determine problem sites that are consuming more than expected resources, thereby eroding the financial value created by RBM.

In addition, the setup module 228 may comprise a user interface for setting up workflow management, e.g., to specify certain workflow parameters such as acceptable waiting time at a state, acceptable aging and lag at a state, escalation criteria, escalation pathway, audit trail requirements, and workflow refresh conditions.

In addition, the setup module 228 may comprise a user interface for setting up user administration, e.g., to specify users 125, roles 418, contact information, security levels, and other user parameters required for system functionality.

As discussed above, after a user 125 has logged in, appropriate functionality may be launched depending on the users role 418 and/or permissions. A user 125 that has been granted executive oversight permissions may be presented with an executive oversight interface to obtain general study status, specific study performance metrics, role-specific metrics, and overall study health score and risks.

The physical architecture 200 may also provide remote monitoring capabilities. In particular, three roles 418 have been discussed above; namely, the medical, central, and statistical monitoring roles 419a-c. According to embodiments, the physical architecture 200 also supports a role 418 specifically for executive oversight. As discussed above, each role 418 may correspond to a monitor module of the physical architecture 200.

The medical monitor 224 may enable a user 125 to examine data at a patient level for patient safety issues, protocol congruence issues (e.g., not following the protocol), compound and therapeutic area congruence issues (e.g., not consistent with known compound class/TA effects), and overall data quality and consistency. The medical monitor 224 may provide the ability to access comprehensive patient level data quickly, intuitively, and in a manner that allows for easy identification of patient safety or data anomaly issues. Accordingly, the medical monitor 224 may comprise sortable, filterable, worklists that allow the medical monitor 224 to quickly navigate to their work queue and focus on patients requiring attention. The medical monitor 224 may additionally or alternatively comprise thumbnail-type mini visuals for patient level data, color-coded to indicate parameters above or below a desired threshold, thereby enabling the user 125 to quickly navigate to problem areas for patients requiring attention. The medical monitor 224 may additionally or alternatively comprise role-specific, interactive visuals over time that allow for easy identification of patient safety or data anomaly issues. The medical monitor 224 may additionally or alternatively comprise ready availability of pre-identified data anomalies through auto-generated queries & triggers, machine learning, etc., for the user 125 to review and take action upon. The medical monitor 224 may additionally or alternatively comprise a built-in Medical Monitor checklist 419a to provide a full audit trail of data reviews performed, actions taken, and follow-up. The medical monitor 224 may additionally or alternatively comprise embedded document links for easy access to important reference documents such as the Study Protocol and the Investigators Brochure. The medical monitor 224 may additionally or alternatively comprise the ability to raise workflow actions 444, embed data and visuals, prescribe specific actions, and route actions to specific individuals/roles.

The medical monitor 224 may expose various capabilities to the user 125 through appropriate user interfaces, e.g., upon launching the medical monitor 224, to view a patient summary, more detailed patient information, and/or workflows for the medical monitor 224.

The central monitor 222 may enable the user 125 to examine data at a site level. For example, the central monitor 222 may allow the user 125 to monitor sites for quality, performance, risk, safety, and optimal resource management. The central monitor 222 may additionally or alternatively triage & prioritize triggers on critical variables and actions raised manually (e.g., via the monitors) to CRAs. The central monitor 222 may additionally or alternatively manage how CRAs resolve actions & triggers. Further, the central monitor 222 may additionally or alternatively follow-up on unresolved/pending actions.

Triggers and actions raised through automated checks or another monitor may go to the central monitor 222. A user 125 acting according to the central monitor role may then triage these actions to the site staff and coordinate site actions. The central monitor 222 may act as the clearinghouse for all actions raised throughout the physical architecture 200. Thus the central monitor 222 may provide users 125 with the ability to access comprehensive site-level data quickly, intuitively, and in a manner that allows for easy identification of site performance, quality, risk, or safety issues.

To enable these capabilities, the central monitor 222 may use a scoring mechanism that categorizes the sites. For example, the central monitor 222 may categorize a site in a readily visualized manner, such as using Red to indicate that a site needs immediate attention, Amber to generally warn about a site, and Green to indicate that a site presents no immediate concerns. Such categorizations may allow a user 125 to quickly focus on problem sites, countries, and/or regions.

Further, the central monitor 222 may provide sortable, filterable, worklists that allow a user 125 to quickly navigate to their work queue and focus on sites requiring attention. The central monitor 222 may also provide workflow visuals that allow the user 125 to quickly identify sites with pending actions, triggers, and workflow items. Further, the aging of workflow actions 444 may be given to the user 125, so that the user 125 may focus on sites with the highest aging.

The central monitor 222 may provide cluster graphs that allow the user 125 to cross-compare sites across various parameters, and quickly identify comparative performance of sites on key measures of risk, safety, performance, and quality. The central monitor 222 may additionally or alternatively provide thumbnail-type mini visuals for key site performance, quality, risk, and safety data that are color-coded to indicate parameters above or below desired thresholds. Thus, the central monitor 222 may allow the user 125 to quickly navigate to the problem sites requiring attention. Thus, the central monitor 222 may provide role-specific, interactive visuals over time that allows for easy identification of site performance, quality, risk, safety or data anomaly issues.

The central monitor 222 may additionally or alternatively make pre-identified data anomalies readily-available to the user 125 through, for example, auto-generated queries, triggers, and machine learning, for the user 125 to review and take action upon. Further, the above-discussed central monitor checklist 419c may provide an audit trail of data reviews performed, actions taken, and follow-ups. Embedded document links may provide easy access to important reference documents such as the Study Protocol, Clinical Monitoring Plan, and Data Management Plan.

The central monitor 222 may also provide the user 125 with the ability to raise workflow actions 444, embed data and visuals, prescribe specific actions, and route actions to specific individuals and/or roles, both known within, and externally to, the physical architecture 200. The central monitor 222 may also provide the user 125 with the ability to package workflow actions 444 to create logical, comprehensive packages 446 of actions either by action needed (e.g., actions requiring site phone call or site email, actions requiring site visit), CRA (actions for a CRA across several investigator sites), region, country, or other grouping attributes.

One or more of the above capabilities may be provided through one or more central monitor 222 user interfaces, e.g., upon launching the central monitor, to perform multivariate comparison of sites, for workflow comparison of sites, view a site summary, perform more detailed site evaluation, and/or examine the workflow of a site.

The statistical monitor 225 may examine data at patient and site level for procedural errors (e.g., not following the protocol), recording errors (e.g., missing data, incorrect data), and/or fraud. Thus, the statistical monitor 225 may provide the user 125 with the ability to detect "strange" patterns in data through examination of outliers, inliers, over-dispersion, under-dispersion, and correlations (to name a few).

The statistical monitor 225 may provide role-specific customer visualizations to enable a user 125 to analyze and explore univariate 355, multivariate 365, and repeated measures 340 data for site and patient data. Such visualizations may allow the user 125 to quickly explore the data and hone in or signals, trends, outliers, and anomalous data. The statistical monitor 225 may additionally or alternatively enable the user 125 to stratify and/or filter data based on demographic patient and site variables and prospective site and patient data, respectively.

The statistical monitor may utilize advanced statistical models, such as Principal Components Analysis (PCA), Mahalanobis Distance Analysis, Benford's Law Analysis, and Linear Regression Analysis, which use advanced statistical methodologies to identify patterns, trends, outliers, fraud, and other anomalous patterns in the data. The statistical monitor 225 may additionally or alternatively use Machine Learning Algorithms for predictive analytics.

The statistical monitor 225 may additionally or alternatively provide a built-in statistical monitor checklist 442c to provide an audit trail of data reviews performed, actions taken, and follow ups. The statistical monitor 225 may additionally or alternatively provide embedded document links for easy access to important reference documents such as the Study Protocol, Statistical Monitoring Plan, and Data Management Plan.

The statistical monitor 225 may additionally or alternatively enable the user 125 to raise workflow actions 444, embed data and visuals, prescribe specific actions, and route actions to the central monitor 222. The statistical monitor 225 may additionally or alternatively enable the user 125 to import qualified, user-defined statistical models for custom analysis of data. The statistical monitor 225 may additionally or alternatively enable the user 125 to view and import site and patient level data for further analysis by statistical software.

One or more of the above statistical monitor 225 capabilities may be provided through one or more statistical monitor 225 user interfaces. For example, the statistical monitor 225 may provide an analysis selector (e.g., a pull-down menu, set of hyperlinks, or other UI element(s)) by which the user 125 may be able to switch between user interfaces. For example, the user 125 may select multivariate 365 or univariate 355 analysis from the analysis selector and in response be presented with corresponding analysis user interface. Similarly, the user 125 may select repeated measures 340 from the analysis selector and be presented with a corresponding user interface.

Although various user interfaces have been described above, additional, fewer, or different interface mechanisms for navigating through the functions of the various monitors are possible. The various monitors 222, 224, 225 may assist users 125 in robustly and simply using the workflow capabilities of the physical architecture 200. These workflows may generated by other users 125 of the system 100 (e.g. a user 125 of the medical monitor 224 may want a safety event reviewed by a project safety officer), may be generated by automated trigger rules (e.g., by the FLDs 450 when a patient's lab test for blood glucose on a particular visit exceeds a given threshold), or may be generated by statistical 350 and machine learning modules 375 (e.g., using the profiling engine 276, upon identifying that data is missing for a particular patient on a particular visit). These workflows may be targeted toward patient, site, and/or study data (i.e., data that crosses multiple patients and/or sites) that needs to be reviewed.

Transactions within the system 100 may be stored and tracked showing up to, and including, a full history to the user 125 when required. Some or groups of these items may be constructed into a workflow for review by one or more of the roles 418. When a workflow is generated, the workflow may maintain a link to the data or action that generated it as well as any follow up actions. Workflow items may be stored and managed in a workflow repository containing, e.g., a unique identifier, source, type, action, and date.

A user 125 may use the medical monitor 224 to review patient workflow, each item reviewed may be passed on for action to a user 125 of the central monitor 222 when action is warranted. Expected follow-ups for a medical monitor 224 user 125 may include an on-site visit, an email and/or telephonic follow-up, an indication that no action is required, and an escalation to a project safety officer.

A user 125 may use the statistical monitor 225 to review data at a protocol level, e.g., to look at model level outputs and well as explore trends at a site and/or patient level. The statistical monitor 225 may, similar to the medical monitor 224, send items to the central monitor 222 for action.

A user 125 may use the central monitor 222 for workflow management. For example, the central monitor 222 may be used to review content from the medical monitor 224 for action, review content from the statistical monitor 225 for action, and/or review site level alerts generated by the FLDs 450 and/or profiling engine 276 for any follow-up action required. The central monitor 222 may also be used to package and manage external workflows to CRA's and/or other users 125.

Figure 11:
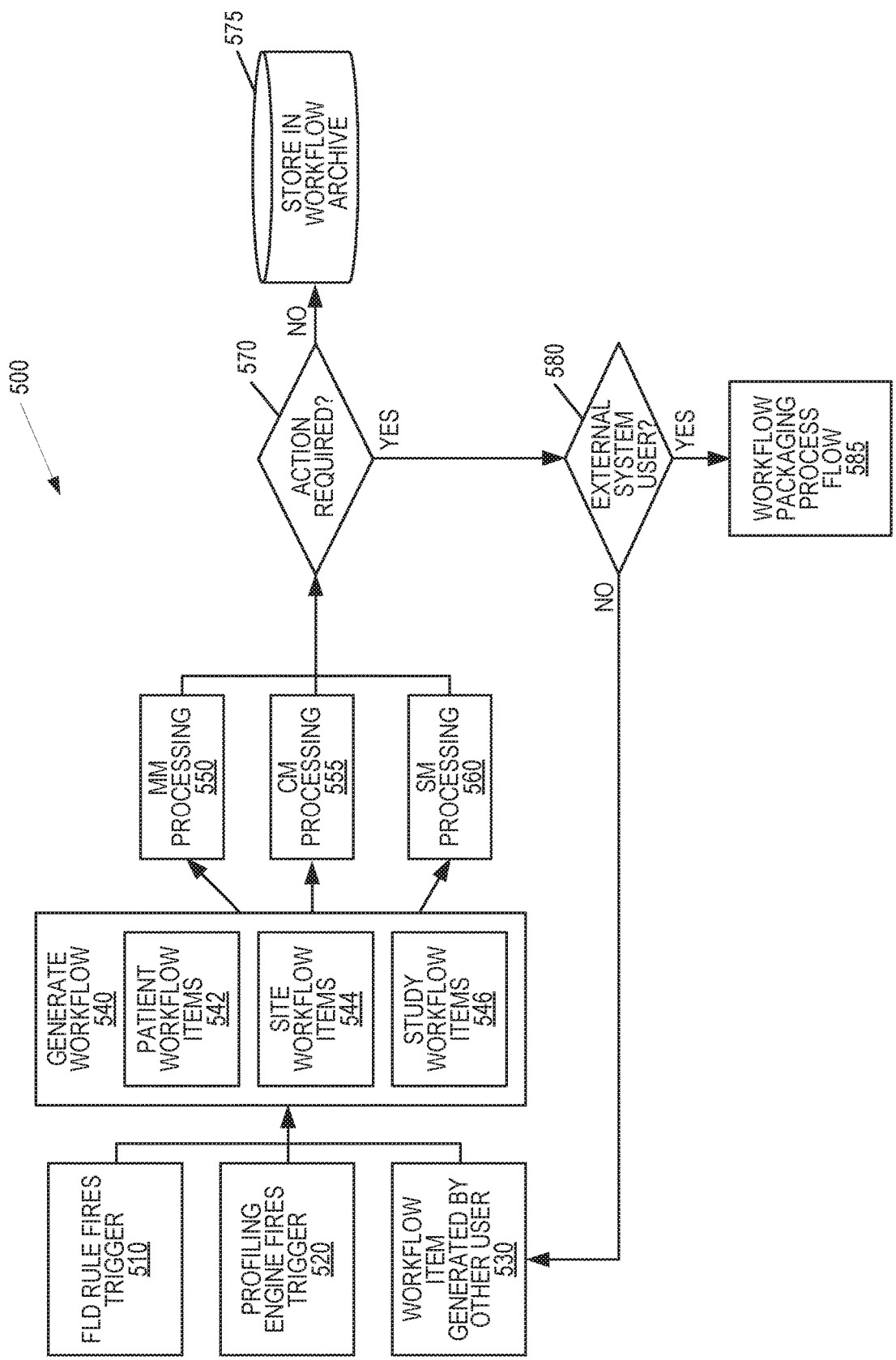
FIG. 11 is a block diagram illustrating an example process for generating a workflow, according to one or more embodiments.

FIG. 11 illustrates an example process 500 for generating a workflow. According to the example process 500, a workflow may be generated in response to a trigger fired by an FLD rule (step 510), the profiling engine (step 520), and/or workflow items generated by users 530. To generate these workflows (step 540), patient, site, and/or study workflow items may be generated or included (steps 542, 544, 546, respectively). These items may be processed by the medical, central, and/or statistical monitors (steps 550, 555, 560), either collectively or respectively). After processing by one or more of the monitors (steps 550, 555, 560), if no action is required (step 570, no), the workflow may be stored in a workflow archive (step 575). If action is required (step 570, yes) by a particular user, and that user is not an external system user (i.e., is a user 125 of the physical architecture 200) (step 580, no), then the action may be treated as a workflow item generated by other users 125, thereby triggering workflow items as discussed above for another user (step 530). If the user 125 is instead an external user (step 580, yes), then workflow packaging (step 585) may be performed for that external user.

Figure 12:
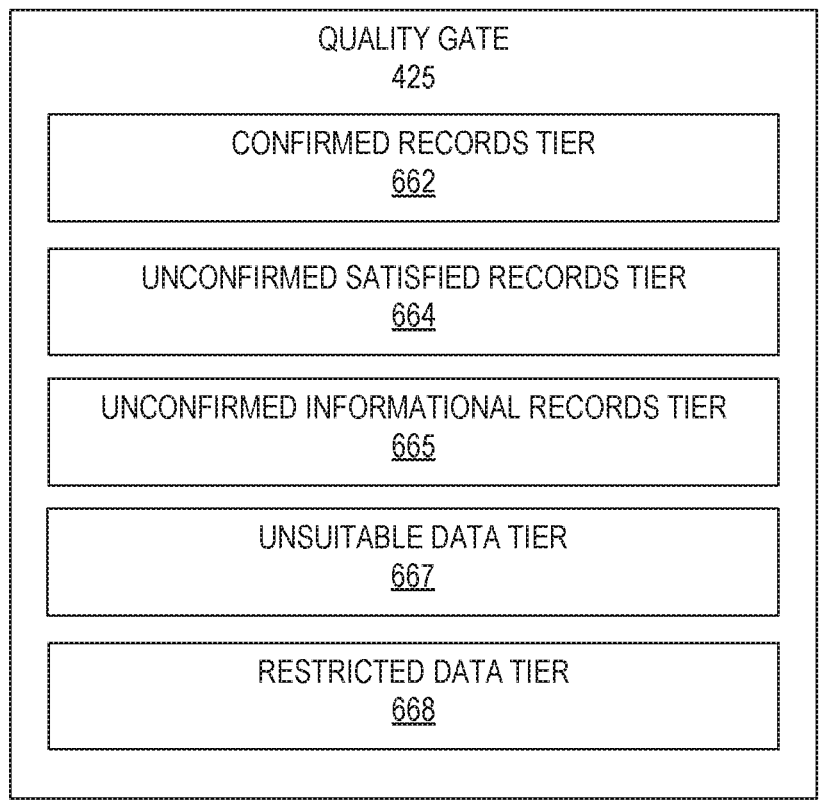
FIG. 12 is a block diagram illustrating an example quality gate, according to one or more embodiments.

The physical architecture 200 may provide the ability to ingest and make available data for analysis in an ongoing and timely manner. To ensure that data is of analysis-level quality, the physical architecture 200 may provide one or more user-configurable quality gates 425 applied to data at any level. For example, a quality gate 425 may be applied at individual data points and/or to an entire feed. A quality gate 425 may operate on data depending on their classification within discrete quality tiers. For example, there may be five tiers of data quality known to the physical architecture 200 as illustrated in the example of FIG. 12. In such an example, a first tier 662 may correspond to confirmed records in which all fields are satisfied without any queries. A second tier 664 may correspond to unconfirmed records in which actions may be triggered, and which may have queries, but mandatory fields are satisfied. A third tier 665 may correspond to unconfirmed records in which some fields are satisfied, but the data is merely informational in nature. A fourth tier 667 may correspond to data that is not suitable for processing. A fifth tier 668 of data may correspond to restricted data that may present a risk of un-blinding the study. The physical architecture 200 may stream the data through one or more quality gates 425 to one or more of the monitors 222, 224, 225 so that corresponding users 125 may examine data that is of decision-making quality.

Data visibility under the control of the physical architecture 200 may be flexible. For example, data may be made available for monitoring in a streaming manner, as and when the data is consumed by the system 100, and/or in a batched manner that allows data to be made available in pre-defined, user-configurable segments. In particular, a data segment may be a collection of visits, data up to a set time point or may be after a particular event has occurred. Data segments allow batches of data to be made visible, for example, to the medical, central, and/or statistical monitor 224, 222, 225 in logical pools that may promote easy of data review and signal detection.

Data segmentation 430, as previously discussed, may allow the physical architecture 200 to anticipate how monitoring activities will be handled and flowed through an organization. The data segmentation 430 within the physical architecture 200 may specify time periods/visits for which data is batched together for the various segments, segment name and number, and/or data included in the various segments. Thus, data segmentation 430 may be user-configurable, and various segments may be defined within the setup module a priori. Further, the segments may be changed during the course of a study, as necessary. The data segments may also be made visually available to a user 125 of the medical monitor 224 to allow filtering by segments.

The physical architecture 200 may comprise a variety of machine learning algorithms as part of an overarching knowledge management engine. Algorithmic data assessment and knowledge management may be handled by role-specific knowledge libraries, machine learning, and/or standard statistical models. Role-specific knowledge libraries may be built and maintained at protocol, program, compound, therapeutic area, and disease levels in order to provide recommendations on critical variables, anticipated safety trends and profiles, meaningful thresholds for triggers and critical variables, and risk indicators. Further, these knowledge libraries may be used to enhance the predictive capabilities of the machine learning engine 274.

Machine learning generally refers to predicting trends and anomalous behavior on patient level data as well as on site performance, quality, risk, and safety. The physical architecture 200 uses accumulated data at a protocol, program, compound, therapeutic area, and/or disease to learn patterns in the data to refine and improve its predictive performance. The machine learning employed by the physical architecture 200 may be passive, in that recommendations are provided to human beings rather than imposing findings automatically. This passive approach may be advantageous to not only effectively deal with processes, but to also effectively manage patient safety. Through this machine learning, input provided by users 125 (and particularly users of the medical, central, and statistical monitors 224, 222, 225) may be used to improve the efficiency of the physical architecture 200 and/or models over time. These machine learning techniques may be particularly useful for detecting similarities (e.g., at the patient, site, protocol, and/or therapeutic area level), learning how the physical architecture 200 is used, detecting missing data, and for fraud detection.

For detecting similarities, clustering methodologies may build profiles of patients and sites based on their shared properties, thereby allowing the physical architecture 200 to learn patterns of both patients and sites within a study. These patterns allow the physical architecture 200 to understand anomalies to the pattern. Various embodiments employ a primarily unsupervised model (e.g., hierarchical clustering). Other embodiments employ a semi-supervised model that allows users 125 (e.g., experts) to verify patterns and clusters created, thereby improving the learning model. Further embodiments learn patterns in the Protocols, Compounds, Therapeutic, and/or Disease areas. Yet further embodiments take an even more supervised approach requiring manual classification of the data. Such machine learning algorithms include random forests and deep learning (neural networks).

Learning how users 125 use the physical architecture 200 may be useful in multiple ways. For example, learning about how the physical architecture 200 is used may be helpful to optimize UI design, enhance users' 125 experience of the system 100, understand common patterns in workflow so that suggested workflow items may be provided, and help drive training of staff and sites where repeated issues are occurring. Further, suggestion engine methodologies may help drive improvements to processes and schemes utilized.

Missing data is a core issue in clinical trials that affects site, power, and validity. Thus, a recommendation engine (not shown) within the physical architecture 200 may suggest items to customers based on a profile of usage, identify gaps in the data, and recognize patterns of incompleteness without recommending the missing data values themselves (e.g. recommending which domains of patient data are usually recorded together). Other embodiments may include data imputation methods, if required.

Fraud detection focuses on outlier/anomaly detection. Unusual patterns of data, even if not driven by fraud, typically need to be investigated. Outliers and anomalies that are difficult for humans to identify from raw data may be easily identified utilizing outlier detection and visualizing them appropriately, e.g., via one or more monitors.

The standard statistical models such as Principle Component Analysis, Mahalonobis Distance analysis, Regression Models, and Benford's Law Model may be pre-loaded in the physical architecture 200, e.g., to allow the user 125 (e.g., via the statistical monitor 225) to detect and understand "strange" patterns in data through examination of outliers, inliers, overdispersion, underdispersion, and correlations (to name a few). Further, various embodiments allow the user 125 to load their own models into the physical architecture 200 so that their preferred analysis may be made available.

The physical architecture 200 may be scalable, and implemented as an integrated SaaS platform for designing, deploying and managing RBM in clinical trials. The physical architecture 200 may provide quick availability and accessibility of data and information for decision making. The physical architecture 200 may also provide the ability to quickly, easily, and intuitively visualize and model subject and operational data from any EDC, Labs, CTMS systems to identify trends, signals, risks and priorities at a point in time, over time, and by various strata (subject demographics, country, region, etc.). Further, the configurable quality gate 425 may help ensure that only decision-quality data is made available, thereby helping to minimize erroneous signal detection.

The physical architecture 200 may be able to quickly and easily convert findings to actions and follow through to closure. Role-based, fully integrated workflows may allow a reviewer of subject/operational data to create actions around the findings, direct the actions to specific individuals and prescribe the type of intervention that is desired for investigating and/or resolving the action and follow the action through to closure. Users 125 may interact with roles 418 and individuals both internal and external to the physical architecture 200.

Users 125 may be able to track value created, e.g., through improved patient safety and data quality, as well as reduction in time and number of site monitoring visits. To ensure that site monitoring visits are used appropriately and judiciously, the physical architecture 200 may track and present comparative metrics on expected, actual, and predicted site monitoring visits, thereby helping to ensure that there is a sharp focus on both the use and value derived from site monitoring visits.

Figure 13:
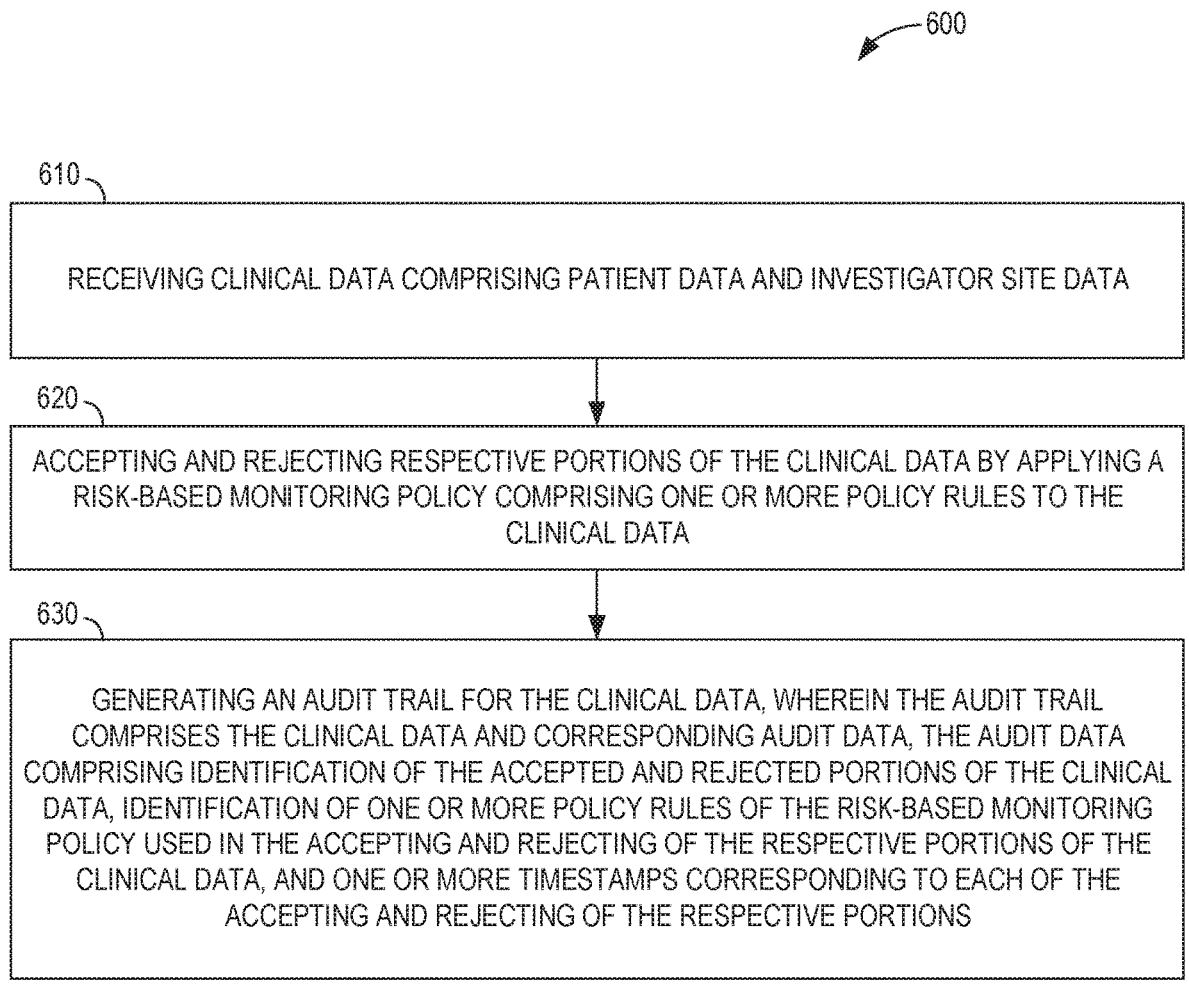
FIG. 13 is a flow diagram illustrating an example method, according to one or more embodiments.

In view of the above, FIG. 13 illustrates an example method 600, implemented by a computing device 110, for generating an audit trail for RBM, according to embodiments of the present disclosure. The method 600 comprises receiving clinical data comprising patient data and investigator site data (block 610). The method 600 further comprises accepting and rejecting respective portions of the clinical data by applying a risk-based monitoring policy comprising one or more policy rules to the clinical data (block 620). The method 600 further comprises generating an audit trail for the clinical data, the audit trail comprising the clinical data and corresponding audit data (block 630). The audit data comprises identification of the accepted and rejected portions of the clinical data, identification of one or more policy rules of the risk-based monitoring policy used in the accepting and rejecting of the respective portions of the clinical data, and one or more timestamps corresponding to each of the accepting and rejecting of the respective portions.

Figure 14:
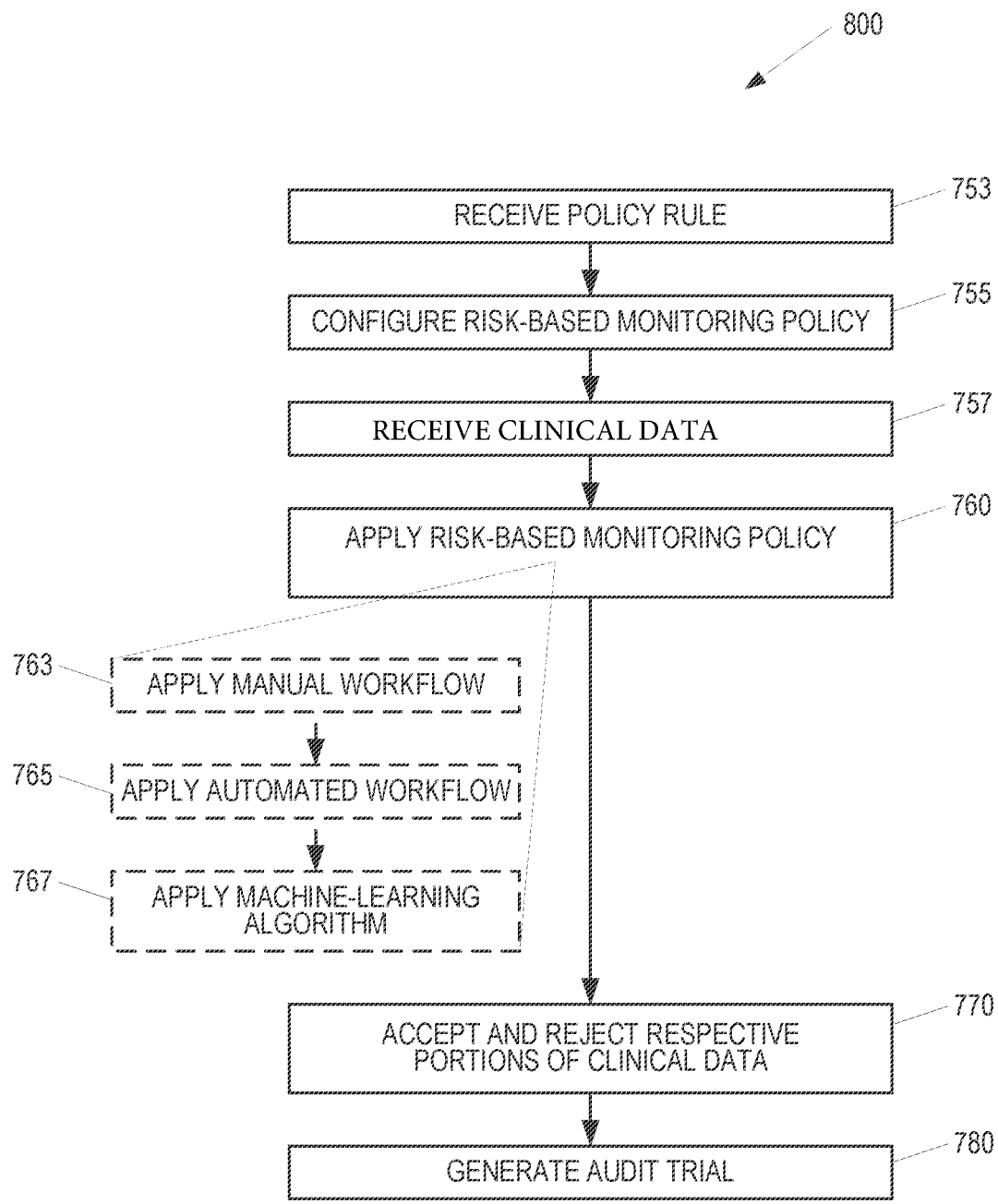
FIG. 14 is a flow diagram illustrating a further example method, according to one or more embodiments.

A more detailed method 800, implemented by a computing device 110, for generating an audit trail for RBM, according to embodiments of the present disclosure, is illustrated in FIG. 14. The method 800 comprises receiving a policy rule from a user 125 of the computing device 110 (e.g., via a user device 115) (block 753). The computing device 110 configures a risk-based monitoring policy using the policy rule (block 755). Accordingly, the risk-based monitoring policy may be configured to include the received policy rule, a different policy rule based on the received policy rule, and/or one or more other policy rules that were previously configured in the computing device 110, according to particular embodiments.

In an embodiment, a policy rule may require segmenting clinical data into a relevant segment and a remainder, identifying the relevant segment as being comprised in one of the accepted and rejected portions; and timestamping one or more of the relevant segment and the remainder. Additionally or alternatively, the policy rule may require review of the clinical data by a medical reviewer and the generating of the audit trail for the clinical data. Additionally or alternatively, the policy rule may require review of the clinical data by a statistical reviewer and the generating of the audit trail for the clinical data.

The method 800 further comprises receiving the clinical data (block 757). The clinical data may comprise patient data and investigator site data, for example. In some embodiments, the patient data comprises, for at least one patient, demographic data, safety data, efficacy data and/or a medical history. Additionally or alternatively, the investigator site data may comprise productivity, quality, risk, and safety metrics for an investigated clinical site.

The method 800 further comprises applying the risk-based monitoring policy to the clinical data (block 760). In some embodiments, applying the risk-based monitoring policy to the clinical data comprises applying a manual workflow to the clinical data (block 763). In some embodiments, applying the risk-based monitoring policy to the clinical data comprises applying a predefined automated workflow to the clinical data (block 765). In some embodiments, applying the risk-based monitoring policy to the clinical data comprises applying a machine learning algorithm to the clinical data (block 767).

The method 800 further comprises accepting and rejecting respective portions of the clinical data (block 770) and generating an audit trail for the clinical data (block 780). According to embodiments, the audit trail may comprise the clinical data and corresponding audit data. The audit data may comprise identification of the accepted and rejected portions of the clinical data, identification of one or more of the policy rules of the risk-based monitoring policy used in the accepting and rejecting of the respective portions of the clinical data, and/or one or more timestamps corresponding to each of the accepting and rejecting of the respective portions. The audit data may additionally or alternatively comprise a digital signature certifying application of a corresponding policy rule identified in the audit data.

Figure 15:
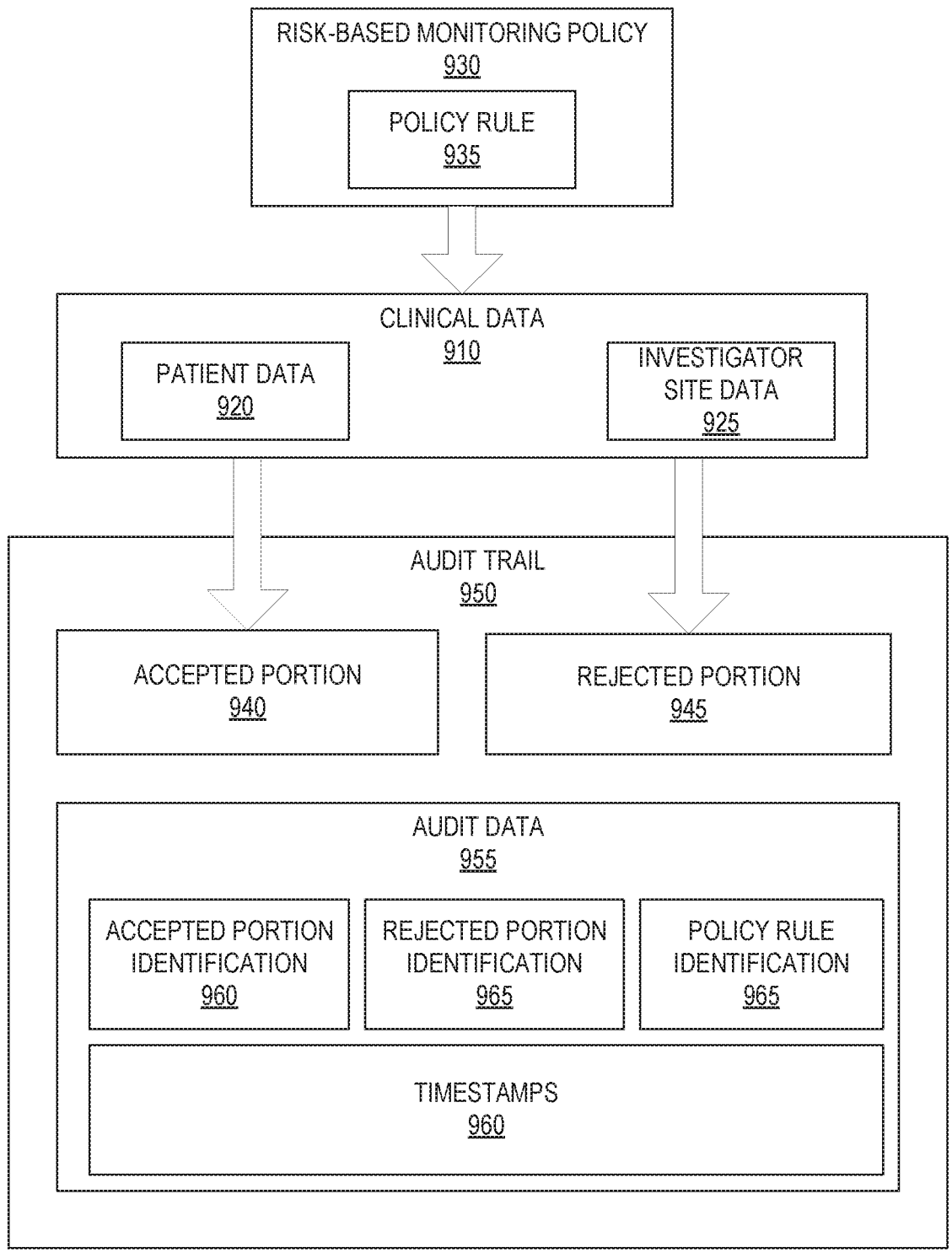
FIG. 15 is a block diagram illustrating an example of generating an audit trail, according to one or more embodiments.

FIG. 15 is a block diagram illustrating an example of the above-discussed generating of an audit trail 950 by the computing device 110. In particular, the computing device 110 applies a risk-based monitoring policy 930 comprising a policy rule 935 to clinical data 910. The clinical data 910 comprises patient data 920 and investigator site data 925. By applying this risk-based monitoring policy, the computing device 110 accepts and rejects respective portions 940, 945 of the clinical data 910, which are included in the audit trail 950 generated by the computing device 110. The audit trail is also generated to include audit data 955 that corresponds to the clinical data 910. In particular, the audit data 955 includes identification of the accepted and rejected portions 960, 965, as well as identification of the policy rule 965 used in the accepting and rejecting. The audit data 955 further comprises one or more timestamps 960 corresponding to each of the accepting and rejecting of the respective portions 940, 945. Accordingly, the audit trail 950 may be used by a user 125 to identify the basis for accepting and rejecting portions 940, 945 of the clinical data 910 (e.g., through identification of the relevant policy rule 935), as well as when the accepting and rejecting took place (e.g., as indicated by the timestamps 960).

Figure 16:
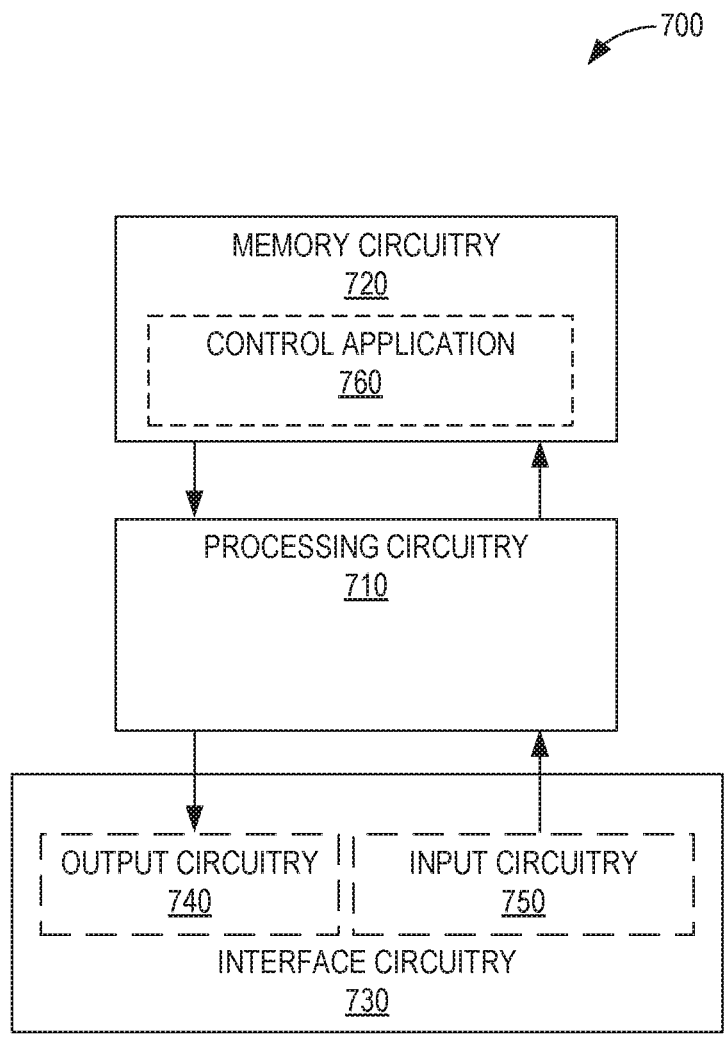
FIG. 16 is a block diagram illustrating example hardware, according to one or more embodiments.

The computing device 110 may be implemented according to the example hardware 700 illustrated in FIG. 16. The example hardware 700 of FIG. 15 comprises processing circuitry 710, memory circuitry 720, and interface circuitry 730. The processing circuitry 710 is communicatively coupled to the memory circuitry 720 and interface circuitry 730, e.g., via one or more buses. The processing circuitry 710 may comprise one or more microprocessors, microcontrollers, hardware circuits, discrete logic circuits, hardware registers, digital signal processors (DSPs), field-programmable gate arrays (FPGAs), application-specific integrated circuits (ASICs), or a combination thereof. For example, the processing circuitry 710 may be programmable hardware capable of executing machine instructions stored as a machine-readable computer program 760 in the memory circuitry 720. The memory circuitry 720 of the various embodiments may comprise any non-transitory machine-readable media known in the art or that may be developed, whether volatile or non-volatile, including but not limited to solid state media (e.g., SRAM, DRAM, DDRAM, ROM, PROM, EPROM, flash memory, solid state drive, etc.), removable storage devices (e.g., Secure Digital (SD) card, miniSD card, microSD card, memory stick, thumb-drive, USB flash drive, ROM cartridge, Universal Media Disc), fixed drive (e.g., magnetic hard disk drive), or the like, wholly or in any combination.

The interface circuitry 730 may be a controller hub configured to control the input and output (I/O) data paths of the computing device 110. Such I/O data paths may include data paths for exchanging signals over a communications network 105 and/or data paths for exchanging signals with a user 125. For example, the interface circuitry 730 may comprise a transceiver configured to send and receive communication signals over one or more of an Ethernet network and an optical network. The interface circuitry 730 may also comprise one or more of a graphics adapter, display port, video bus, touchscreen, graphical processing unit (GPU), display port, Liquid Crystal Display (LCD), and Light Emitting Diode (LED) display, for presenting visual information to a user 125. The interface circuitry 730 may also comprise one or more of a pointing device (such as a mouse, stylus, touchpad, trackball, pointing stick, joystick), touchscreen, microphone for speech input, optical sensor for optical recognition of gestures, and keyboard for text entry.

The interface circuitry 730 may also comprise input circuitry 750 and output circuitry 740. For example, the output circuitry 740 may comprise a transmitter configured to send communication signals over the communications network 105, whereas the input circuitry 750 may comprise a receiver configured to receive communication signals over the communications network 105. Thus, the interface circuitry 730 may be implemented as a unitary physical component, or as a plurality of physical components that may be contiguously or separately arranged, any of which may be communicatively coupled to any other, or may communicate with any other via the processing circuitry 710. Similarly, the output circuitry 740 may comprise a display, whereas the input circuitry 750 may comprise a keyboard. Other examples, permutations, and arrangements of the above and its equivalents will be readily apparent to those of ordinary skill.

The processing circuitry 710 may be configured to receive clinical data 910 comprising patient data 920 and investigator site data 925. The processing circuitry 710 may be further configured to accept and reject respective portions 940, 945 of the clinical data 910 by applying a risk-based monitoring policy 930 comprising one or more policy rules 935 to the clinical data 910. The processing circuitry 710 may be further configured to generate an audit trail 950 for the clinical data 910. The audit trail 950 may comprise the clinical data 910 and corresponding audit data 955. The audit data 955 may comprise identification of the accepted and rejected portions 960, 965 of the clinical data 910, identification of one or more of the policy rules 965 of the risk-based monitoring policy 930 used in the accepting and rejecting of the respective portions 940, 945 of the clinical data 910, and one or more timestamps 960 corresponding to each of the accepting and rejecting of the respective portions 940, 945.

Figure 17:
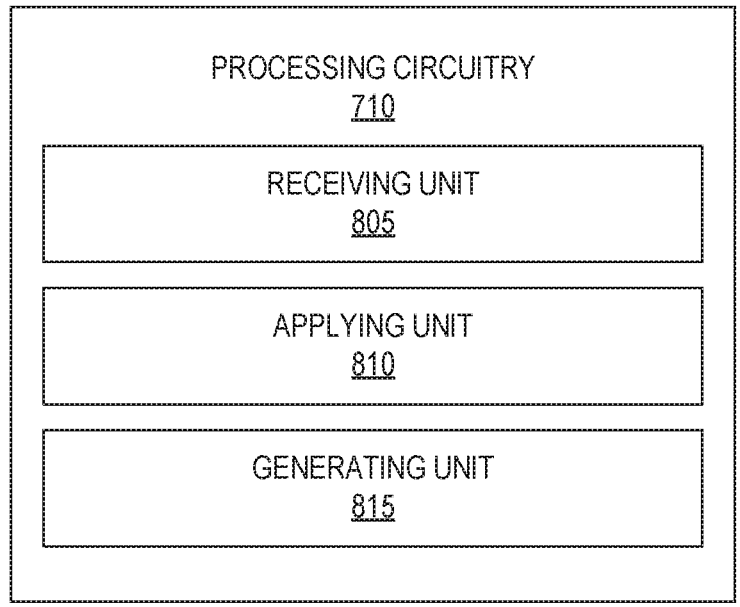
FIG. 17 is a block diagram illustrating example processing circuits comprising a plurality of physical units, according to one or more embodiments.

Other embodiments of the present disclosure include the example processing circuitry 710 of the computing device 110 as illustrated in FIG. 17. The processing circuitry 710 comprises a plurality of communicatively coupled physical units. In particular, the processing circuitry 710 comprises a receiving unit 805, an applying unit 810, and a generating unit 815. The receiving unit 805 is configured to receive clinical data 910 comprising patient data 920 and investigator site data 925. The applying unit 810 is configured to accept and reject respective portions 940, 945 of the clinical data 910 by applying a risk-based monitoring policy 930 comprising one or more policy rules 935 to the clinical data 910. The generating unit 815 is configured to generate an audit trail 950 for the clinical data 910. The audit trail 950 may comprise the clinical data 910 and corresponding audit data 955. The audit data 955 may comprise identification of the accepted and rejected portions 960, 965 of the clinical data 910, identification of one or more of the policy rules 965 of the risk-based monitoring policy 930 used in the accepting and rejecting of the respective portions 940, 945 of the clinical data 910, and one or more timestamps 960 corresponding to each of the accepting and rejecting of the respective portions 940, 945.

Figure 18:
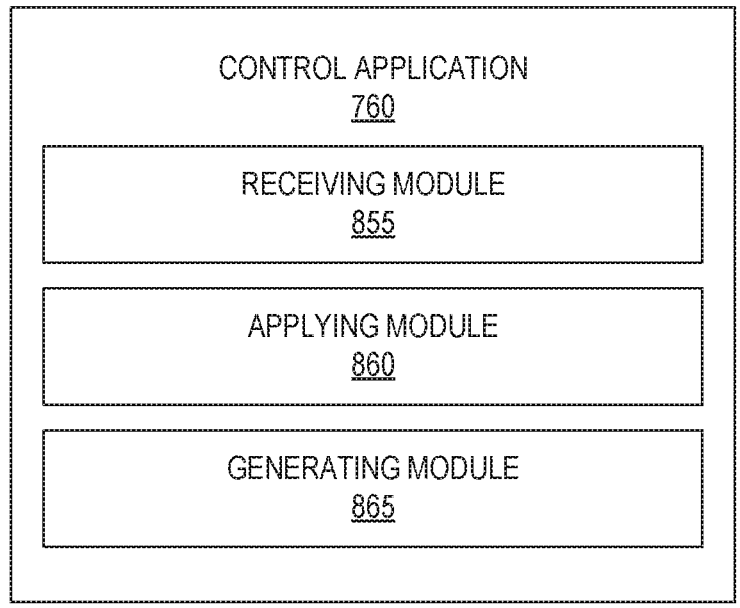
FIG. 18 is a block diagram illustrating an example control program comprising a plurality of software modules, according to one or more embodiments.

Other embodiments of the present disclosure include the example control software 760 of computing device 110, as illustrated in FIG. 18. The control software 760 of FIG. 18 comprises a plurality of software modules. In particular, this control software 760 comprises a receiving module 855, an applying module 860, and a generating module 865. The receiving module 855 is configured to receive clinical data 910 comprising patient data 920 and investigator site data 925. The applying module 860 is configured to accept and reject respective portions 940, 945 of the clinical data 910 by applying a risk-based monitoring policy 930 comprising one or more policy rules 935 to the clinical data 910. The generating module 865 is configured to generate an audit trail 950 for the clinical data 910. The audit trail 950 may comprise the clinical data 910 and corresponding audit data 955. The audit data 955 may comprise identification of the accepted and rejected portions 960, 965 of the clinical data 910, identification of one or more of the policy rules 965 of the risk-based monitoring policy 930 used in the accepting and rejecting of the respective portions 940, 945 of the clinical data 910, and one or more timestamps 960 corresponding to each of the accepting and rejecting of the respective portions 940, 945.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method, implemented by a computing device, for generating an audit trail for monitoring clinical data, the method comprising:
   receiving clinical data comprising patient data and investigator site data, wherein the investigator site data comprises safety metrics;
   accepting and rejecting respective portions of the clinical data by applying a risk-based monitoring policy comprising one or more policy rules to the clinical data, wherein applying the risk-based monitoring policy comprises applying, to the clinical data, a machine-learning algorithm, wherein applying the machine-learning algorithm comprises:
   learning, over time, patterns in the patient data and investigator site data of the clinical data;
   receiving, over time, input from users regarding risk indicators in the learned patterns; and
   maintaining, over time, a knowledge library based on the learned patterns and received input, wherein the accepting and rejecting of the portions of the clinical data is based on the maintained knowledge library;
   generating an audit trail for the clinical data based on applying the risk-based monitoring policy to the clinical data, the audit trail comprising the clinical data and corresponding audit data, the audit data comprising:
   identification of the accepted and rejected portions of the clinical data;
   identification of one or more of the policy rules of the risk-based monitoring policy used in the accepting and rejecting of the respective portions of the clinical data;
   one or more timestamps corresponding to when each of the accepting and rejecting of the respective portions took place.

2. The method of claim 1, wherein applying the risk-based monitoring policy comprises applying, to the clinical data, one or more of a manual workflow or a predefined automated workflow.

3. The method of claim 1, wherein the one or more policy rules comprises a policy rule that requires:
   segmenting the clinical data into a relevant segment and a remainder;
   identifying the relevant segment as being comprised in one of the accepted and rejected portions; and
   timestamping one or more of the relevant segment and the remainder.

4. The method of claim 1, wherein the audit data further comprises a digital signature certifying application of a corresponding policy rule identified in the audit data.

5. The method of claim 1, wherein the patient data comprises, for at least one patient, demographic data, safety data, efficacy data and a medical history.

6. The method of claim 1, wherein the investigator site data comprises productivity, quality, and risk for an investigated clinical site.

7. The method of claim 1, further comprising configuring the risk-based monitoring policy by receiving a policy rule of the one or more policy rules from a user of the computing device.

8. The method of claim 1, wherein the one or more of the policy rules comprises a policy rule that requires review of the clinical data by a medical reviewer and the generating of the audit trail for the clinical data.

9. The method of claim 1, wherein the one or more of the policy rules comprises a policy rule that requires review of the clinical data by a statistical reviewer and the generating of the audit trail for the clinical data.

10. A computing device for generating an audit trail for monitoring clinical data, the computing device comprising:
    interface circuitry configured to exchange signals over one or more data paths of the computing device;
    processing circuitry communicatively coupled to the interface circuitry and configured to:
        receive clinical data comprising patient data and investigator site data via the interface circuitry, wherein the investigator site data comprises safety metrics;
        accept and reject respective portions of the clinical data by applying a risk-based monitoring policy comprising one or more policy rules to the clinical data, wherein applying the risk-based monitoring policy comprises applying, to the clinical data, a machine-learning algorithm, wherein applying the machine-learning algorithm comprises:
            learning, over time, patterns in the patient data and investigator site data of the clinical data;
            receiving, over time, input from users regarding risk indicators in the learned patterns; and
            maintaining, over time, a knowledge library based on the learned patterns and received input, wherein the accepting and rejecting of the portions of the clinical data is based on the maintained knowledge library;
        generate an audit trail for the clinical data based on applying the risk-based monitoring policy to the clinical data, the audit trail comprising the clinical data and corresponding audit data;
    wherein the audit data comprises:
        identification of the accepted and rejected portions of the clinical data;
        identification of one or more policy rules of the risk-based monitoring policy used in the accepting and rejecting of the respective portions of the clinical data;
        one or more timestamps corresponding to when each of the accepting and rejecting of the respective portions took place.

11. The computing device of claim 10, wherein applying the risk-based monitoring policy comprises applying, to the clinical data, one or more of a manual workflow or a predefined automated workflow.

12. The computing device of claim 10, wherein the one or more policy rules comprises a policy rule that requires:
    segmenting the clinical data into a relevant segment and a remainder;
    identifying the relevant segment as being comprised in one of the accepted and rejected portions; and
    timestamping one or more of the relevant segment and the remainder.

13. The computing device of claim 10, wherein the audit data further comprises a digital signature certifying application of a corresponding policy rule identified in the audit data.

14. The computing device of claim 10, wherein the patient data comprises, for at least one patient, demographic data, safety data, efficacy data and a medical history.

15. The computing device of claim 10, wherein the investigator site data comprises productivity, quality, and risk for an investigated clinical site.

16. The computing device of claim 10, wherein the processing circuitry is further configured to configure the risk-based monitoring policy by receiving a policy rule of the one or more policy rules from a user of the computing device.

17. The computing device of claim 10, wherein the one or more of the policy rules comprises a policy rule that requires review of the clinical data by a medical reviewer and the generating of the audit trail for the clinical data.

18. The computing device of claim 10, wherein the one or more of the policy rules comprises a policy rule that requires review of the clinical data by a statistical reviewer and the generating of the audit trail for the clinical data.

19. A non-transitory computer readable medium storing a computer program product for controlling a programmable computing device in a communication network, the computer program product comprising software instructions that, when run on the programmable computing device, cause the programmable computing device to:
    receive clinical data comprising patient data and investigator site data via interface circuitry, wherein the investigator site data comprises safety metrics;
    accept and reject respective portions of the clinical data by applying a risk-based monitoring policy comprising one or more policy rules to the clinical data, wherein applying the risk-based monitoring policy comprises applying, to the clinical data, a machine-learning algorithm, wherein applying the machine-learning algorithm comprises:
        learning, over time, patterns in the patient data and investigator site data of the clinical data;
        receiving, over time, input from users regarding risk indicators in the learned patterns; and
        maintaining, over time, a knowledge library based on the learned patterns and received input, wherein the accepting and rejecting of the portions of the clinical data is based on the maintained knowledge library;
    generate an audit trail for the clinical data based on applying the risk-based monitoring policy to the clinical data, the audit trail comprising the clinical data and corresponding audit data, the audit data comprising:
        identification of the accepted and rejected portions of the clinical data;
        identification of one or more policy rules of the risk-based monitoring policy used in the accepting and rejecting of the respective portions of the clinical data;
        one or more timestamps corresponding to when each of the accepting and rejecting of the respective portions took place.

* * * * *